US012333235B2

(12) United States Patent
Souche et al.

(10) Patent No.: US 12,333,235 B2
(45) Date of Patent: Jun. 17, 2025

(54) DISABILITY-ORIENTED FONT GENERATOR

(71) Applicant: Accenture Global Solutions Limited, Dublin (IE)

(72) Inventors: Christian Souche, Valbonne (FR); Edouard Mathon, Antibes (FR); Ji Tang, Valbonne (FR)

(73) Assignee: Accenture Global Solutions Limited, Dublin (IE)

( * ) Notice: Subject to any disclaimer, the term of this patent is extended or adjusted under 35 U.S.C. 154(b) by 103 days.

(21) Appl. No.: 17/453,449

(22) Filed: Nov. 3, 2021

(65) Prior Publication Data

US 2023/0134226 A1 May 4, 2023

(51) Int. Cl.
*G06F 40/109* (2020.01)
*A61B 3/032* (2006.01)
(Continued)

(52) U.S. Cl.
CPC .......... *G06F 40/109* (2020.01); *G06F 40/103* (2020.01); *G06F 40/166* (2020.01); *A61B 3/0066* (2013.01); *A61B 3/032* (2013.01); *G06T 11/001* (2013.01); *G09B 21/008* (2013.01); *G09G 5/24* (2013.01)

(58) Field of Classification Search
CPC ...... G06F 40/109; A61B 3/032; G09B 21/008
See application file for complete search history.

(56) References Cited

U.S. PATENT DOCUMENTS 7,272,785 B2 * 9/2007 Fukuda ................. G06F 40/166
  707/E17.121
7,659,914 B1 * 2/2010 Rostami ................. G06T 11/60
  345/636

(Continued)

FOREIGN PATENT DOCUMENTS

CN      104156971 A  * 11/2014
JP      2004348211 A * 12/2004  .......... G06F 17/212
JP      2010154546 A    7/2010

OTHER PUBLICATIONS

Juangallostra, Bites of Code, Converting images to ASCII art (Part 11), May 27, 2017, 20 pages, https://bitesofcode.wordpress.com/2017/05/27/converting-images-to-ascii-art-part-2/ (Year: 2017).*

(Continued)

*Primary Examiner* — Benjamin Smith
(74) *Attorney, Agent, or Firm* — POLSINELLI PC

(57) ABSTRACT

In some implementations, a font generator device may receive input text that includes one or more characters. The font generator device may generate a disability-oriented font based on one or more parameters that relate to a vision deficiency, wherein the disability-oriented font is readable by users that have the vision deficiency and unreadable by users that do not have the vision deficiency. The font generator device may transform the one or more characters included in the input text into the disability-oriented font. The font generator device may generate an output that represents the input text using the disability-oriented font based on transforming the one or more characters included in the input text into the disability-oriented font.

20 Claims, 12 Drawing Sheets
(4 of 12 Drawing Sheet(s) Filed in Color)

(51) Int. Cl.
    *G06F 40/103*     (2020.01)
    *G06F 40/166*     (2020.01)
    *G09B 21/00*     (2006.01)
    *A61B 3/00*     (2006.01)
    *G06T 11/00*     (2006.01)
    *G09G 5/24*     (2006.01)

(56) References Cited

U.S. PATENT DOCUMENTS

| | | | | |
|---|---|---|---|---|
| 7,898,553 | B2* | 3/2011 | Smith | G06F 16/583 |
| | | | | 345/629 |
| 8,494,859 | B2* | 7/2013 | Said | G06F 40/12 |
| | | | | 715/239 |
| 8,990,224 | B1* | 3/2015 | Ouellette | G06Q 10/10 |
| | | | | 707/754 |
| 9,072,434 | B2* | 7/2015 | Thibos | A61B 3/028 |
| 9,241,620 | B1* | 1/2016 | Kockan | G06F 3/0482 |
| 9,952,658 | B2* | 4/2018 | Hosabettu | G06F 3/005 |
| 10,168,854 | B2* | 1/2019 | Kockan | G06F 3/0481 |
| 10,444,934 | B2* | 10/2019 | Bradley | G06F 40/117 |
| 10,592,401 | B2* | 3/2020 | Kobayashi | G06F 8/38 |
| 10,713,416 | B2* | 7/2020 | Eaton | G06F 3/04842 |
| 10,769,827 | B1* | 9/2020 | Amerige | G06V 10/56 |
| 10,809,877 | B1* | 10/2020 | Bradley | G10L 15/22 |
| 10,928,978 | B2* | 2/2021 | Bradley | G06F 3/04817 |
| 11,029,815 | B1* | 6/2021 | Bradley | G10L 15/22 |
| 11,030,438 | B2* | 6/2021 | Quinteros | A61B 3/10 |
| 11,061,532 | B2* | 7/2021 | Bradley | G06F 3/0482 |
| 11,132,495 | B1* | 9/2021 | Doke | G06F 3/04855 |
| 11,222,615 | B2* | 1/2022 | ShafieiBavani | G09G 5/37 |
| 11,270,603 | B1* | 3/2022 | Bansal | G09B 21/009 |
| 11,423,206 | B2* | 8/2022 | Kraus | G06F 40/103 |
| 11,461,494 | B2* | 10/2022 | Nambannor Kunnath | |
| | | | | G06F 40/197 |
| 11,475,794 | B2* | 10/2022 | Kusmec-Aguilar | G09B 23/28 |
| 11,978,139 | B2* | 5/2024 | Nykyforov | G06N 20/00 |
| 12,094,357 | B2* | 9/2024 | Kusmec-Aguilar | G09B 23/28 |
| 2004/0143430 | A1* | 7/2004 | Said | G06F 40/12 |
| | | | | 704/2 |
| 2004/0145592 | A1* | 7/2004 | Twersky | G06T 11/00 |
| | | | | 345/619 |
| 2005/0041040 | A1* | 2/2005 | Fukuda | G06T 5/30 |
| | | | | 345/619 |
| 2006/0280338 | A1* | 12/2006 | Rabb | G09B 21/006 |
| | | | | 704/271 |
| 2009/0079668 | A1* | 3/2009 | Liu | G09G 3/006 |
| | | | | 345/30 |
| 2015/0009474 | A1* | 1/2015 | Thibos | A61B 3/032 |
| | | | | 351/233 |
| 2016/0029884 | A1* | 2/2016 | Kockan | G09G 5/00 |
| | | | | 351/239 |
| 2016/0093080 | A1* | 3/2016 | Tumanov | G06T 11/60 |
| | | | | 345/589 |
| 2016/0246762 | A1* | 8/2016 | Eaton | G06F 3/04847 |
| 2016/0274656 | A1* | 9/2016 | Hosabettu | G06F 3/005 |
| 2017/0177166 | A1* | 6/2017 | Kockan | A61B 3/0025 |
| 2017/0213323 | A1* | 7/2017 | Kobayashi | G06F 8/38 |
| 2017/0269816 | A1* | 9/2017 | Bradley | G06F 40/14 |
| 2018/0253216 | A1* | 9/2018 | Beene | G09B 21/007 |
| 2019/0108200 | A1* | 4/2019 | Nambannor Kunnath | |
| | | | | G09G 5/30 |
| 2019/0287420 | A1* | 9/2019 | Kusmec-Aguilar | G09B 23/28 |
| 2019/0294861 | A1* | 9/2019 | Quinteros | G06V 40/166 |
| 2019/0346921 | A1* | 11/2019 | Caride | G06F 3/013 |
| 2020/0174916 | A1* | 6/2020 | Kobayashi | G06T 11/60 |
| 2020/0334411 | A1* | 10/2020 | Patel | G06F 40/143 |
| 2020/0371669 | A1* | 11/2020 | Bradley | G06F 3/04817 |
| 2021/0043109 | A1* | 2/2021 | Mese | G09B 5/00 |
| 2021/0157474 | A1* | 5/2021 | Bradley | G10L 13/027 |
| 2021/0303770 | A1* | 9/2021 | Doke | G06F 40/30 |
| 2021/0327301 | A1* | 10/2021 | Kusmec-Aguilar | G09B 23/28 |
| 2022/0036217 | A1* | 2/2022 | Nykyforov | G06V 10/22 |
| 2022/0036611 | A1* | 2/2022 | Nykyforov | G06F 40/109 |
| 2022/0057651 | A1* | 2/2022 | Segre | G02C 7/042 |
| 2022/0138402 | A1* | 5/2022 | Kraus | G06N 3/08 |
| | | | | 715/269 |
| 2022/0201362 | A1* | 6/2022 | Plug | G06V 20/42 |
| 2022/0365668 | A1* | 11/2022 | Ekron | G06F 40/186 |
| 2022/0365760 | A1* | 11/2022 | Ekron | G06F 16/9538 |
| 2022/0365987 | A1* | 11/2022 | Ekron | G06F 16/958 |
| 2022/0365989 | A1* | 11/2022 | Ekron | G06F 40/186 |
| 2022/0365999 | A1* | 11/2022 | Ekron | G06F 40/14 |
| 2022/0366002 | A1* | 11/2022 | Ekron | G06F 40/109 |
| 2022/0366003 | A1* | 11/2022 | Ekron | G06F 16/957 |
| 2022/0366131 | A1* | 11/2022 | Ekron | G06F 8/34 |
| 2023/0004622 | A1* | 1/2023 | Ekron | G06F 3/013 |
| 2023/0029752 | A1* | 2/2023 | Szuchmacher | G06N 20/00 |
| 2023/0032425 | A1* | 2/2023 | Ekron | G06F 3/013 |
| 2023/0097039 | A1* | 3/2023 | Kusmec-Aquilar | G09B 23/28 |
| | | | | 359/885 |
| 2023/0122824 | A1* | 4/2023 | Narayanan | G10L 13/08 |
| | | | | 704/200 |

OTHER PUBLICATIONS

Jonh, "Generate ANSI-/Ascii-art version images/Gifs in your terminal", Sep. 28, 2021, 10 pages, https://golangexample.com/generate-ansi-ascii-art-version-images-gifs-in-your-terminal/ (Year: 2021).*
Danielle Bragg, Shiri Azenkot, and Adam Tauman Kalai. 2016. Reading and Learning Smartfonts. In Proceedings of the 29th Annual Symposium on User Interface Software and Technology (UIST '16). Association for Computing Machinery, New York, NY, USA, 391-402. https://doi.org/10.1145/2984511.2984554 (Year: 2016).*
Danielle Bragg, 2017. Designing and Evaluating Livefonts. In Proceedings of the 30th Annual ACM Symposium on User Interface Software and Technology (UIST '17). Association for Computing Machinery, New York, NY, USA, 481-492. https://doi.org/10.1145/3126594.3126660 (Year: 2017).*
Charles Bigelow, Typeface features and legibility research, Vision Research, vol. 165, 2019, pp. 162-172, ISSN 0042-6989, https://doi.org/10.1016/j.visres.2019.05.003. (Year: 2019).*
I. Dela Torre and I. Khaliq, "A Study on Accessibility in Games for the Visually Impaired," 2019 IEEE Games, Entertainment, Media Conference (GEM), New Haven, CT, USA, 2019, pp. 1-7, doi: 10.1109/GEM.2019.8811534. (Year: 2019).*
Iqbal, Muhammad waseem & Shahzad, Syed Khuram & Ahmad, Nadeem & Amelio, Alessia & Brodic, Darko. (2018). Adaptive Interface for Color-blind People in Mobilephones. 8 pages. 10.1109/ICACS.2018.8333488. (Year: 2018).*
Juangallostra, Bites of Code, Converting images to ASCII art (Part 1), Jan. 19, 2017, 23 pages, https://bitesofcode.wordpress.com/2017/01/19/converting-images-to-ascii-art-part-1/ (Year: 2017).*
Juangallostra, Bites of Code, Converting images to ASCII art (Part 2), May 27, 2017, 20 pages, https://bitesofcode.wordpress.com/2017/05/27/converting-images-to-ascii-art-part-2/ (Year: 2017).*
Bragg et al., "Reading and Learning Smart Fonts", User Interface Software and Technology, ACM, Oct. 2016, pp. 391-402, XP058299689, DOI: 10.1145/2984511.2984554 ISBN: 978-1-4503-4189-9.
Extended European Search Report for Application No. EP22174778.5, mailed on Nov. 7, 2022, 10 pages.
Iqbal et al., "Adaptive Interface for Color-Blind People in Mobile-Phones", International Conference On Advancements In Computational Sciences (ICACS), Feb. 2018, IEEE, pp. 1-8, XP033345011, DOI: 10.1109/ICACS.2018.8333488.
Torre et al., "A Study on Accessibility in Games for the Visually Impaired", IEEE Games, Entertainment, Media Conference (GEM), Jun. 2019, pp. 1-7, XP033604520, DOI: 10.1109/GEM.2019.8811534.

* cited by examiner

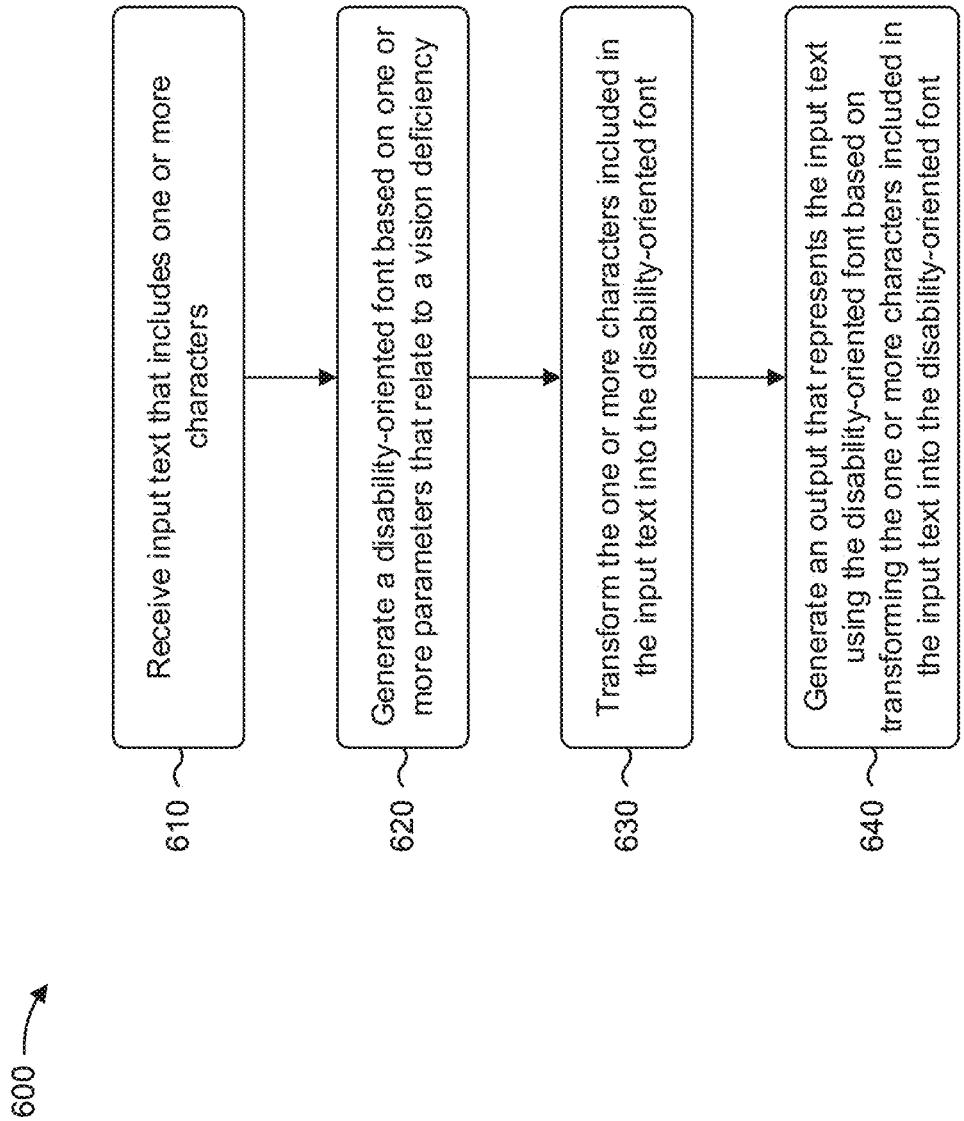

DISABILITY-ORIENTED FONT GENERATOR

BACKGROUND

Vision deficiency, also known as vision impairment or vision loss, generally refers to a decreased ability to see. For example, one common vision deficiency is myopia, or near-sightedness, which is an eye disorder in which light focuses in front of retina, which causes distant objects to appear blurry while close objects may appear normal. In many cases, myopia can be corrected with eyeglasses, contact lenses, or refractive surgery. However, severe myopia is associated with an increased risk of retinal detachment, cataracts, and glaucoma, while uncorrected myopia can lead to vision loss to a degree that may not be correctable with usual techniques. Another common vision deficiency is color blindness, which refers to a decreased ability to see color and/or differences in color. In some cases, color blindness can impair daily activities such as selecting ripe fruit, choosing clothing, or reading traffic lights and/or make a person ineligible for certain jobs such as an aircraft pilot, a train driver, or another profession that relies upon color vision to perform work. Furthermore, a person with corrected myopia, corrected hyperopia, or other vision corrections may experience vision impairment (e.g., blurred vision or a decreased ability to see and/or differentiate color) in certain settings when the corrective measures are not in use (e.g., while engaged in a sporting activity or in bed, among other examples).

SUMMARY

Some implementations described herein relate to a method. The method may include receiving, by a font generator device, input text that includes one or more characters. The method may include generating, by the font generator device, a disability-oriented font based on one or more parameters that relate to a vision deficiency, wherein the disability-oriented font is readable by users that have the vision deficiency and unreadable by users that do not have the vision deficiency. The method may include transforming, by the font generator device, the one or more characters included in the input text into the disability-oriented font. The method may include generating, by the font generator device, an output that represents the input text using the disability-oriented font based on transforming the one or more characters included in the input text into the disability-oriented font.

Some implementations described herein relate to a font generator device. The font generator device may include one or more memories and one or more processors coupled to the one or more memories. The one or more processors may be configured to receive input text that includes one or more characters. The one or more processors may be configured to generate a disability-oriented font based on one or more parameters that relate to a vision deficiency, wherein the disability-oriented font is readable by users that have the vision deficiency and unreadable by users that do not have the vision deficiency. The one or more processors may be configured to transform the one or more characters included in the input text into the disability-oriented font. The one or more processors may be configured to generate content that is targeted at users that have the vision deficiency, wherein the content includes an output that represents the input text using the disability-oriented font that is readable only by users that have the vision deficiency and unreadable by users that do not have the vision deficiency.

Some implementations described herein relate to a non-transitory computer-readable medium that stores a set of instructions for a font generator device. The set of instructions, when executed by one or more processors of the font generator device, may cause the font generator device to receive input text that includes one or more characters. The set of instructions, when executed by the one or more processors of the font generator device, may cause the font generator device to generate a disability-oriented font based on one or more parameters that relate to a vision deficiency, wherein the disability-oriented font is readable by users that have the vision deficiency and unreadable by users that do not have the vision deficiency. The set of instructions, when executed by the one or more processors of the font generator device, may cause the font generator device to transform the one or more characters included in the input text into the disability-oriented font. The set of instructions, when executed by the one or more processors of the font generator device, may cause the font generator device to generate an output to identify one or more users that have the vision deficiency by representing the input text using the disability-oriented font based on transforming the one or more characters included in the input text into the disability-oriented font.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

FIG. 6 is a flowchart of an example process relating to a disability-oriented font generator that may generate a font that is only readable by users with a vision deficiency.

DETAILED DESCRIPTION

Figure 1:
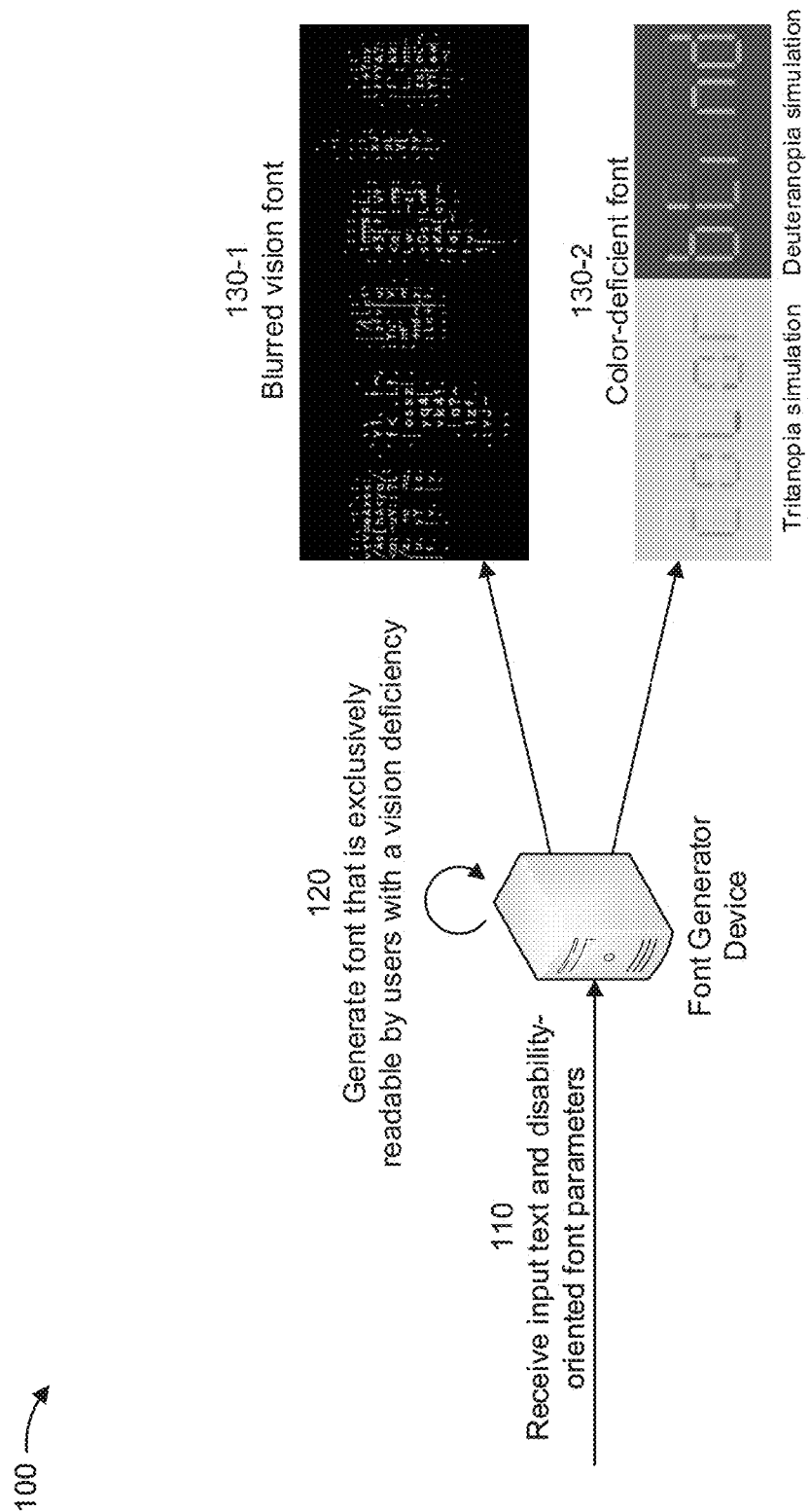
FIG. 1 is a diagram of an example implementation of a disability-oriented font generator that may generate one or more fonts that are only readable by users with a vision deficiency.

The following detailed description of example implementations refers to the accompanying drawings. The same reference numbers in different drawings may identify the same or similar elements.

There are more than one billion people (or approximately 15 percent of the global population) with disabilities that do not have content targeted to them based on their disabilities. For example, in context with some implementations described herein, a disability may generally refer to any condition that makes it more difficult for a person to do certain activities or effectively interact with the surrounding world. In various cases, the conditions (or impairments) may be cognitive, developmental, intellectual, mental, physical, sensory, environmental, or a combination of multiple factors. Although there has been significant progress in increasing accessibility to people with movement disabilities, generating content that is targeted toward users with specific disabilities continues to pose challenges. For example, because computer interfaces often solicit visual input and/or provide visual feedback, a significant challenge in increasing computer accessibility relates to creating digital content that is tailored to people with vision impairments. For example, users that have certain vision disabilities or vision deficiencies (e.g., blurred vision caused by myopia or hyperopia or a color vision deficiency caused by a type of color blindness) may experience information losses (e.g., a decreased ability to perceive text texture and/or text color) when reading, watching, or otherwise interacting with digital content. However, existing techniques to improve accessibility for visually disabled users tend to focus on improving the perceptibility of existing content. For example, large fonts, displays with a high dots per inch, high-contrast themes, icons that are augmented with auditory feedback, and screen magnifying software are some techniques that are used to improve access by people with mild to moderate vision impairments, while screen reader software or refreshable braille display may be used to enable computer interactions by people with severe vision impairments. Accordingly, existing accessibility techniques tend to fall short in enabling an ability to create content that includes messaging or information that is specifically targeted to users with vision deficiencies. For example, existing accessibility techniques are unable to generate content that is perceptible only by people with a specific disability, which hinders capabilities to convey information that is specifically targeted at users with specific disabilities, identify or diagnose users with specific disabilities, and/or filter out users without specific disabilities.

Some implementations described herein relate to a disability-oriented font generator that may generate one or more fonts that are readable by users with a specific vision deficiency and unreadable by users without the specific vision deficiency. For example, in some implementations, the disability-oriented font generator may generate a blurred vision font that is exclusively readable by users with uncorrected blurred vision (e.g., users with myopia or hyperopia that do not wear eyeglasses or contact lenses and/or users subject to a vision impacted situation that causes blurred vision, such as looking through frosted glass) and unreadable by users with corrected blurred vision or normal vision. In particular, as described in further detail herein, a font generator device may receive an input text string and/or an input image that contains an input text string, and the font generator device may transform the input text string into a sequence of character clouds that represent the input text string in a way that is only readable by users with uncorrected blurred vision. For example, in some implementations, each character cloud may include various alphanumeric characters, symbols, and/or white spaces that are spatially arranged to represent the simulated appearance of a corresponding character in the input text string to a user with blurred vision or a user in a vision-impacted situation that causes blurred vision. For example, as described herein, users with blurred vision and users without blurred vision may both have a depreciated ability to read text that is rendered in the blurred vision font, but text in the blurred vision font will be unreadable for users without blurred vision while still being readable for users with blurred vision. In this way, rather than generating the blurred vision font to improve readability for users with blurred vision, the font generator device may generate the character clouds to render the input text string in the blurred vision font in order to convey information that is specifically targeted at users with uncorrected blurred vision, enable identification or diagnosis of users with uncorrected blurred vision, and/or filter out users without blurred vision.

Additionally, or alternatively, in some implementations, the disability-oriented font generator may generate a color-deficient font that is exclusively readable by users with a color vision deficiency or users in a primary color deficiency situation (e.g., color blind users that experience deuteranopia, tritanopia, and/or protanopia and/or users in a color-deficient environment or situation, such as a pure monochromatic light environment). In particular, as described in further detail herein, the font generator device may receive an input text string and/or an input image that contains an input text string, and the font generator device may map each character in the input text string to a character template that includes various strokes that can be used to represent different characters (e.g., similar to a seven-segment figure used to represent different numbers on a digital clock). For example, a background color may be selected for the color-deficient font, and the font generator device may search one or more color spaces to identify a first color group that includes colors that are close to the background color in a color-deficient color space but different from the background color in a normal color space. Furthermore, the font generator device may search the color space(s) to identify a second color group that includes colors that are close to the background color in the color-deficient color space and different from the background color in the normal color space. Accordingly, the font generator device may generate an output image in which the character templates mapped to the input text string are rendered over the background color, and further in which the colors in the first color group and the second color group are used to color the various strokes of the character templates such that the text in the final output image is exclusively readable by users with a color vision deficiency (e.g., color blindness) and/or users in a vision-impacted situation associated with a primary color deficiency. For example, as described herein, users with a color vision deficiency and users without a color vision deficiency may both have a depreciated ability to read text that is rendered in the color-deficient font, but text rendered in the color-deficient vision font will be unreadable for users without a color vision deficiency while still being readable for users with the color vision deficiency. In this way, rather than generating the color-deficient font to improve readability for users with a color vision deficiency, the font generator device may generate the color-deficient font to convey information that is specifically targeted at users with a color vision deficiency and/or users in a vision-impacted situation associated with a primary color deficiency, identify or diagnose users with a color vision deficiency and/or users in a vision-impacted situation associated with a primary color deficiency, and/or filter out users without a color vision deficiency and/or users that are not in a vision-impacted situation associated with a primary color deficiency.

FIG. 1 is a diagram of an example implementation 100 associated with a disability-oriented font generator. As shown in FIG. 1, example implementation 100 includes a font generator device that may generate one or more fonts that are only readable by users with a vision deficiency. The font generator device is described in more detail below in connection with FIG. 4 and FIG. 5.

As shown in FIG. 1, and by reference number 110, the font generator device may receive input text and one or more parameters that relate to generating a disability-oriented font (e.g., a font that is exclusively readable by users that have a specific vision deficiency). For example, as described in further detail below with reference to FIGS. 2A-2D, the font generator device may be configured to generate a blurred vision font that is readable by users with uncorrected blurred vision (e.g., users with myopia, also known as near-sightedness, users with hyperopia, also known as far-sightedness, and/or users in a vision-impacted situation causing blurred vision). Furthermore, as described herein, the blurred vision font may be unreadable or difficult to read by users without blurred vision or with corrected blurred vision (e.g., eyeglasses, contact lenses, and/or refractive surgery). Additionally, or alternatively, as described in further detail below with reference to FIGS. 3A-3D, the font generator device may be configured to generate a color-deficient font that is readable by users with a specific color vision deficiency (e.g., color blindness, such as deuteranopia, tritanopia, or protanopia) and/or users that are in a vision-impacted situation that may cause or otherwise be associated with a primary color deficiency (e.g., a pure monochromatic light environment, such as a darkroom). Furthermore, the color-deficient font may be unreadable or difficult to read by users without color blindness, users with a different color blindness type, and/or users that are not in a situation where color vision may be impacted. For example, as described in further detail elsewhere herein, the font generator device may receive input text presented in an original font and/or an image that includes input text presented in an original font, and the one or more parameters received by the font generator device may be used to generate the blurred vision font (e.g., an alternative characters list for populating one or more character clouds and/or parameters to configure a stroke thickness, spacing, and/or other visual detail(s) associated with the character clouds). Additionally, or alternatively, the font generator device may receive one or more parameters that may be used to generate the color-deficient font (e.g., a background color and a color blindness type that may define one or more color spaces to be searched for different color groups based on the background color).

As further shown in FIG. 1, and by reference number 120, the font generator device may generate a font that is exclusively readable by users with a specific vision deficiency. For example, in order to generate the blurred vision font that is only readable by users with uncorrected blurred vision, the font generator device may map each character in the input string to a character cloud that includes various alternative characters that are spatially dispersed in a manner that reflects how the respective character would appear to a user with uncorrected blurred vision. For example, an alternative character list may include various lowercase letters, uppercase letters, numbers, symbols, and/or a blank space, among other examples, each of which may be associated with a value (e.g., an average red-green-blue (RGB) value) that represents the whiteness or darkness of the alternative character. Accordingly, the font generator device may determine a mapping from a whitest character in the alternative character list to a darkest character in the alternative character list, and may use the mapping to generate a sequence of character clouds that represent the original input text string based on the relative whitenesses and/or darknesses in each pixel of an image that reflects a simulated appearance of the input text string to a user with uncorrected blurred vision. For example, as shown by reference number 130-1, the blurred vision font may represent the input text string "myopia" using a first character cloud that includes various alternative characters that are spatially dispersed to represent the letter "m", a second character cloud that includes various spatially dispersed alternative characters to represent the letter "y", a third character cloud that includes various spatially dispersed alternative characters to represent the letter "o", and so on. In this way, the blurred vision font shown by reference number 130-1 may represent the input text string using character clouds that are easy to read for a person with uncorrected blurred vision (e.g., spherical blurred vision caused by myopia or hyperopia), but the character clouds may be difficult to read or decipher for a person without blurred vision and/or with uncorrected blurred vision.

Additionally, or alternatively, as described herein, the font generator device may generate a font that is exclusively readable by users with a specific color vision deficiency (e.g., a color blindness type or other situation where color vision may be impacted). For example, a color blind user may have deuteranopia, also called green-blind (a decreased ability to see or distinguish red and green pigments), or a color blind user may have tritanopia (a decreased ability to see or distinguish blue and yellow pigments) or protanopia, also called red-blindness (a state in which red cones are absent from the eye, leaving only cones that absorb blue and green light). In general, the colors that can be seen and/or distinguished by a user with a color vision deficiency may vary depending on the color deficiency type, whereby the font generator device may generate the color-deficient font using color groups that are selected based on the color deficiency type. For example, in order to generate the color-deficient font in a manner that is only readable by users with a specific color blindness type, the font generator device may map each character in the input string to a character template that includes various strokes that can be used to represent different characters (e.g., a character template with strokes that are arranged in a shape like the number 8 on a digital alarm clock may be used to represent any letter in the set {a, e, o, s, u} or a number or symbol).

Accordingly, the font generator device may receive or select an appropriate background color for the sequence of character templates mapped to the input string, and may search a normal color space and a color-deficient color space associated with the applicable color blindness type to identify a first color group to be applied to strokes that are to blend in with the background and a second color group to be applied to strokes that are to be colored to depict the corresponding character. For example, as shown by reference number 130-2, the color-deficient font generated for a user with tritanopia may include a pink background, and character templates that are mapped to the text string "color" are colored with one or more colors that would be perceived as blending into the background for a user with tritanopia. Furthermore, the strokes that forms the letters of the word "color" are colored with blue or similar colors that would be perceived as distinguishable from the background color and the strokes that are perceived as blending into the background. Furthermore, different colors may be chosen for the background and/or the color groups that are used to color the character templates for a different color blindness type (e.g., as shown by the deuteranopia simulation in FIG. 1). In this way, the color-deficient font(s) shown by reference number 130-2 may represent the input text string using character templates that are rendered against a background and colored with different color combinations that make the text string easily readable for a person with a specific color vision deficiency or a person in a specific color vision impacted situation but otherwise very difficult to read for a person without a color vision deficiency and/or user with a different color blindness type.

Accordingly, as described herein, the font generator device may generate one or more disability-oriented fonts that are exclusively readable by users with a specific vision deficiency (e.g., easily readable by users with the specific vision deficiency and very difficult to read by users without the specific vision deficiency), which may enable targeted messaging that is directed toward users with the specific vision deficiency. For example, the disability-oriented fonts may be used to render text on one or more display devices or print media, which may be used to identify users with undiagnosed or uncorrected vision deficiencies (e.g., based on the users having the ability to read the text). Additionally, or alternatively, the disability-oriented fonts may include information or messaging to solicit feedback and/or elicit behavior from users with specific vision deficiencies, recommend treatment options and/or corrective measures that may improve visual acuity or daily functioning (e.g., recommending that a user who can read the text obtain an eye exam for the targeted vision deficiency), and/or to filter out users that may not have a vision deficiency, among other examples.

As indicated above, FIG. 1 is provided as an example. Other examples may differ from what is described with regard to FIG. 1.

FIGS. 2A-2D are diagrams of an example implementation 200 of a disability-oriented font generator. As shown in FIGS. 2A-2D, example implementation 200 includes a font generator device and a display device. The font generator device and the display device are described in more detail below in connection with FIG. 4 and FIG. 5. In general, as described herein, the font generator device that may generate a font that is only readable by users with uncorrected blurred vision, and the display device may present one or more character clouds in the font that is only readable by users with uncorrected blurred vision. For example, myopia (or near-sightedness) is generally the most common vision deficiency, and can lead to physical ailments (e.g., eyestrain and/or headaches) and/or cause more severe vision impairments over the long term when left uncorrected (e.g., vision loss to a degree that is not correctable by eyeglasses, contact lenses, or other typical corrective measures). Myopia is typically diagnosed by an eye care professional (e.g., an optometrist or ophthalmologist), but some uncorrected myopic people or myopic children may not discover their near-sightedness in time to take appropriate corrective measures to prevent more severe problems. Accordingly, the font generator device described herein may be configured to generate the font that is only readable by myopic users in order to aid with recognizing or identifying (e.g., diagnosing) myopic users and/or delivering targeted messaging to myopic users. However, it will be appreciated that the techniques described herein may be similarly applied to generate a font that is readable by users with any suitable type of blurred vision, which may include myopia, hyperopia (far-sightedness), and/or blurred vision caused by other factors such as looking through frosted glass or having foreign particles (e.g., dust) in the eyes, among other examples.

Figure 2A:
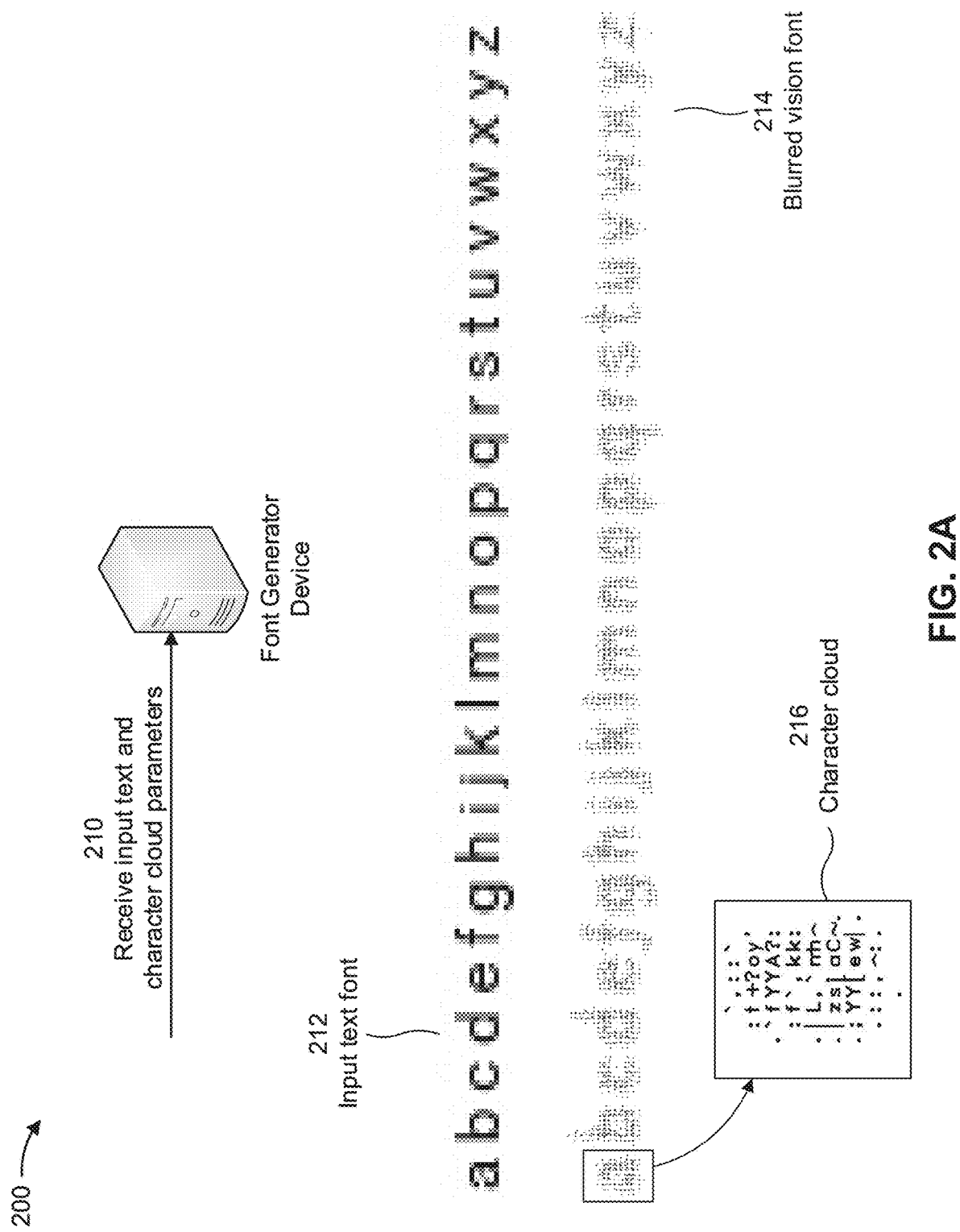
FIGS. 2A-2D are diagrams of an example implementation of a disability-oriented font generator that may generate a font that is only readable by users with uncorrected blurred vision.

For example, as shown in FIG. 2A, and by reference number 210, the font generator device may receive input text and one or more character cloud parameters that are used to generate a blurred vision font in which to present the input text. In some implementations, as shown by reference number 212, the input text may include a text string that is presented in an original font, or the input to the font generator device may include an image that contains the text string presented in the original input text font. As described in further detail herein, and as shown by reference number 214, the font generator device may generate the blurred vision font as various character clouds that each represent a corresponding character in the input text font, where the character clouds are generated based on the character cloud parameters input to the font generator device. For example, the character cloud parameters may include an alternative character list (e.g., a set of characters that are used to form the character clouds), a character cloud thickness (e.g., a desired weight for the characters represented by the character clouds and/or the alternative characters that form the character clouds), a character cloud spacing (e.g., a desired spacing between adjacent character clouds and/or the alternative characters that form the character clouds), and/or a color in which to render the character clouds, among other examples. In some implementations, the one or more character cloud parameters (e.g., character cloud stroke thickness, character cloud spacing, alternative character list, and/or color) may be configurable and/or dependent on the input text font, which may be selected to be readable for users with uncorrected blurred vision (otherwise the blurred vision font may be unreadable for users with uncorrected blurred vision). Accordingly, as described herein, the character clouds that make up the blurred vision font are not fixed, and the character clouds may be composed of different characters depending on the parameters related to the character cloud stroke thickness, the character cloud spacing, the alternative character list, color, and/or the original input text font, among other examples (e.g., to incorporate variation into the blurred vision font). For example, reference number 216 illustrates a character cloud mapped to the letter "a", where various characters are spatially dispersed to represent the letter "a" in a way that is easy to read for a user with uncorrected blurred vision and difficult to read by a user with corrected blurred vision and/or a user without blurred vision.

Figure 2B:
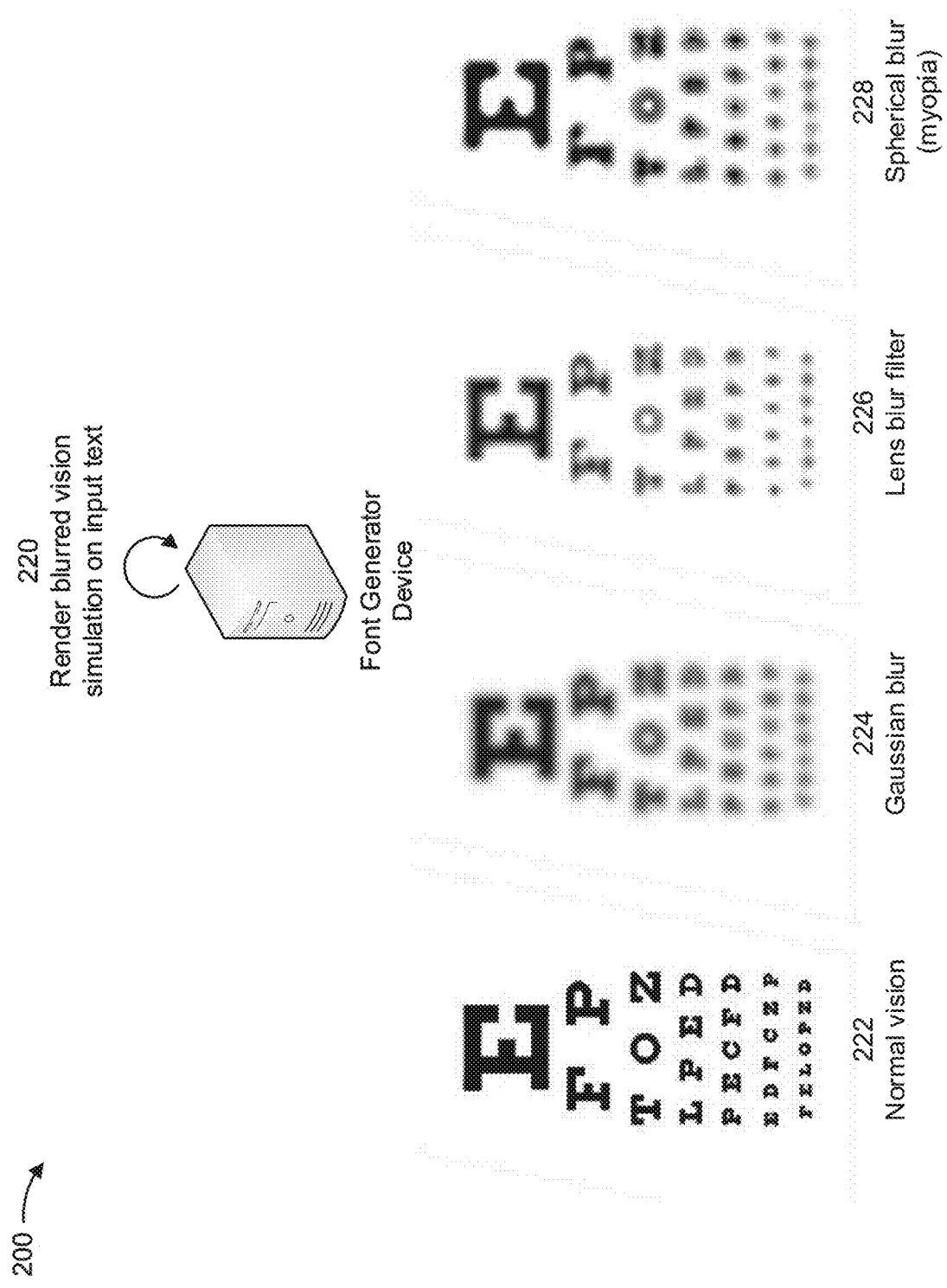

As shown in FIG. 2B, and by reference number 220, the font generator device may render a blurred vision simulation on the input text in order to generate a simulated image that reflects how the input text would appear to a user with uncorrected blurred vision. For example, in FIG. 2B, reference number 222 illustrates input text as it would appear to a person with normal vision. In the illustrated example, the input text includes text that is structured like an eye chart that may be used to test a person for myopia or hyperopia, where the input text includes various characters that are arranged on different lines with varying character sizes used on the different lines. However, because a myopic or hyperopic user would have a decreased ability to see, the readability of the input text would generally be reduced for a myopic or hyperopic user or a user with blurred vision caused by other (e.g., environmental) factors. Accordingly, in some implementations, the font generator device may render the blurred vision simulation by applying one or more digital effects or other image processing techniques to produce an image that represents how the input text would be perceived by a user with blurred vision. For example, reference number 224 represents the appearance of the input text after applying a Gaussian blur to the input text, and reference number 226 represents the appearance of the input text after applying a lens blur filter to the input text. In the context of a blurred vision font for a user with uncorrected myopia, a myopic user normally has spherical blurred vision, whereby the blurred vision simulation that is rendered on the input text may apply a spherical blur to the input text as it appears to be a person with normal vision in order to derive an image that depicts how the same input text would appear to a person with uncorrected myopia. In this way, as described in further detail herein, the blurred vision simulation may be used to generate the character clouds that are mapped to the input text such that a sequence of character clouds output by the font generator may appear very similar to the blurred vision simulation rendered on the input text.

Figure 2C:
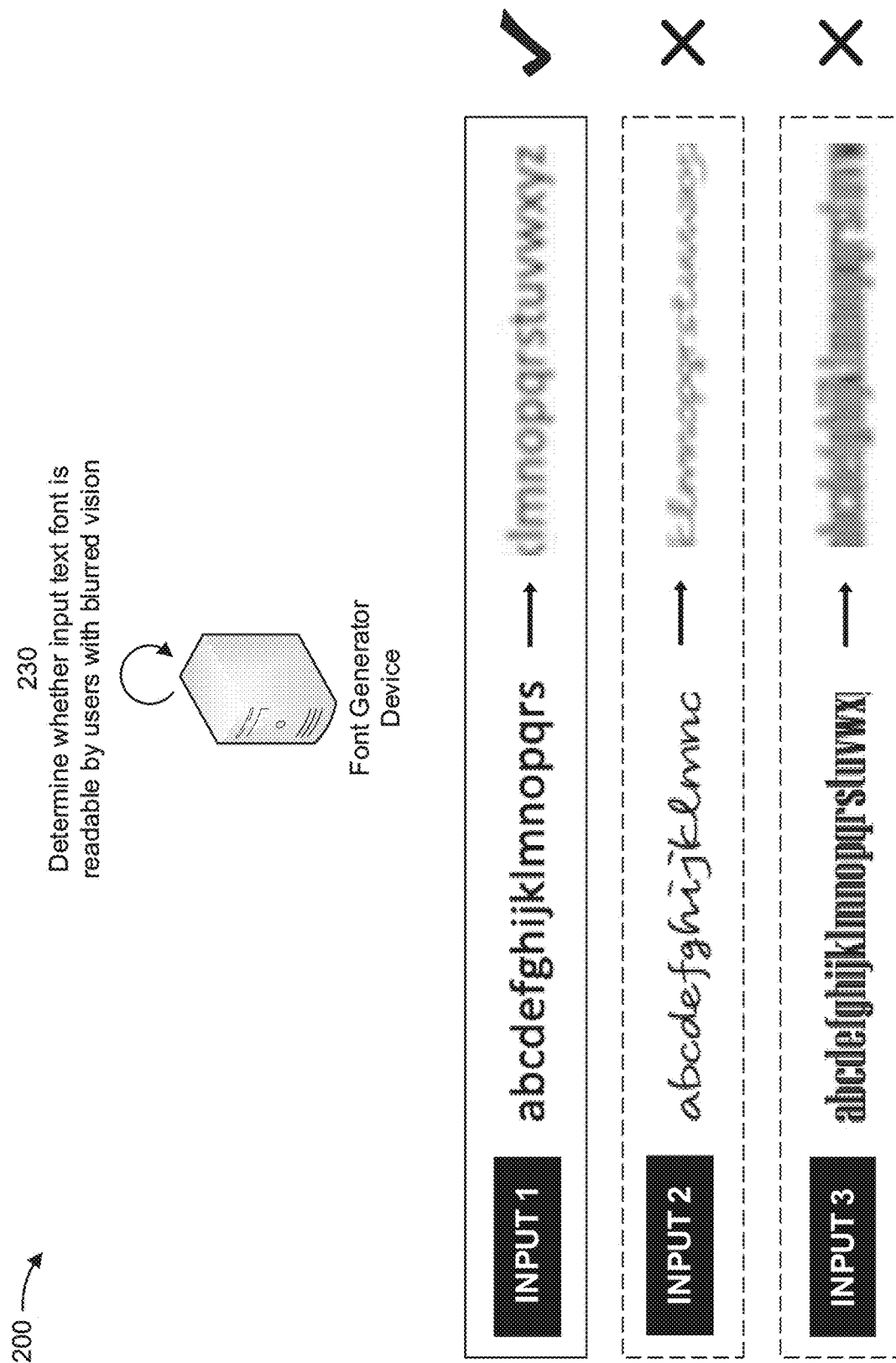

As shown in FIG. 2C, and by reference number 230, the font generator device may perform a readability check to determine whether the input text font is readable by users with uncorrected blurred vision prior to generating the blurred vision font based on the blurred vision simulation. For example, if the original input text font is unreadable by users with uncorrected blurred vision, a blurred vision font that includes character clouds generated based on the blurred vision simulation is highly likely to be unreadable by users with uncorrected blurred vision. Accordingly, because the purpose of the blurred vision font is to be easily readable by users with uncorrected blurred vision but unreadable by corrected myopic or hyperopic users or users without blurred vision, the font generator device may perform the readability check to verify that the input text font is readable by users with uncorrected blurred vision. For example, FIG. 2C illustrates a first example (shown as "Input 1") where a myopia simulation rendered on a first input text font is determined to be readable by myopic users, but other input text fonts (shown as "Input 2" and "Input 3") are determined to be unreadable by myopic users. In some implementations, the font generator device may use one or more artificial intelligence or machine learning models that are trained to predict whether the simulated appearance of the input text font to a user with uncorrected blurred vision is readable or unreadable. For example, in some implementations, the artificial intelligence or machine learning models may generate an output that indicates a predicted interpretation of the text by a user with uncorrected blurred vision and/or a metric that indicates a confidence level in the predicted interpretation. Accordingly, based on the font generator device determining that the predicted interpretation of the text is correct and/or that the confidence level satisfies (e.g., equals or exceeds) a threshold, the font generator device may proceed to generate the blurred vision font based on the blurred vision simulation. Alternatively, based on the font generator device determining that the predicted interpretation of the text is incorrect and/or that the confidence level fails to satisfy the threshold, the font generator device may abort the blurred vision font generation process and/or test other parameters to generate the blurred vision font. For example, the font generator device may render a blurred vision simulation and perform another readability check using a different font that has a clearer differentiation between characters or a larger spacing between characters, a larger font size, capital letters versus lower case letters, and/or other parameters that may improve readability after a spherical blur or other suitable image processing technique is applied to simulate the appearance of the input text font to an uncorrected myopic or hyperopic user.

Figure 2D:
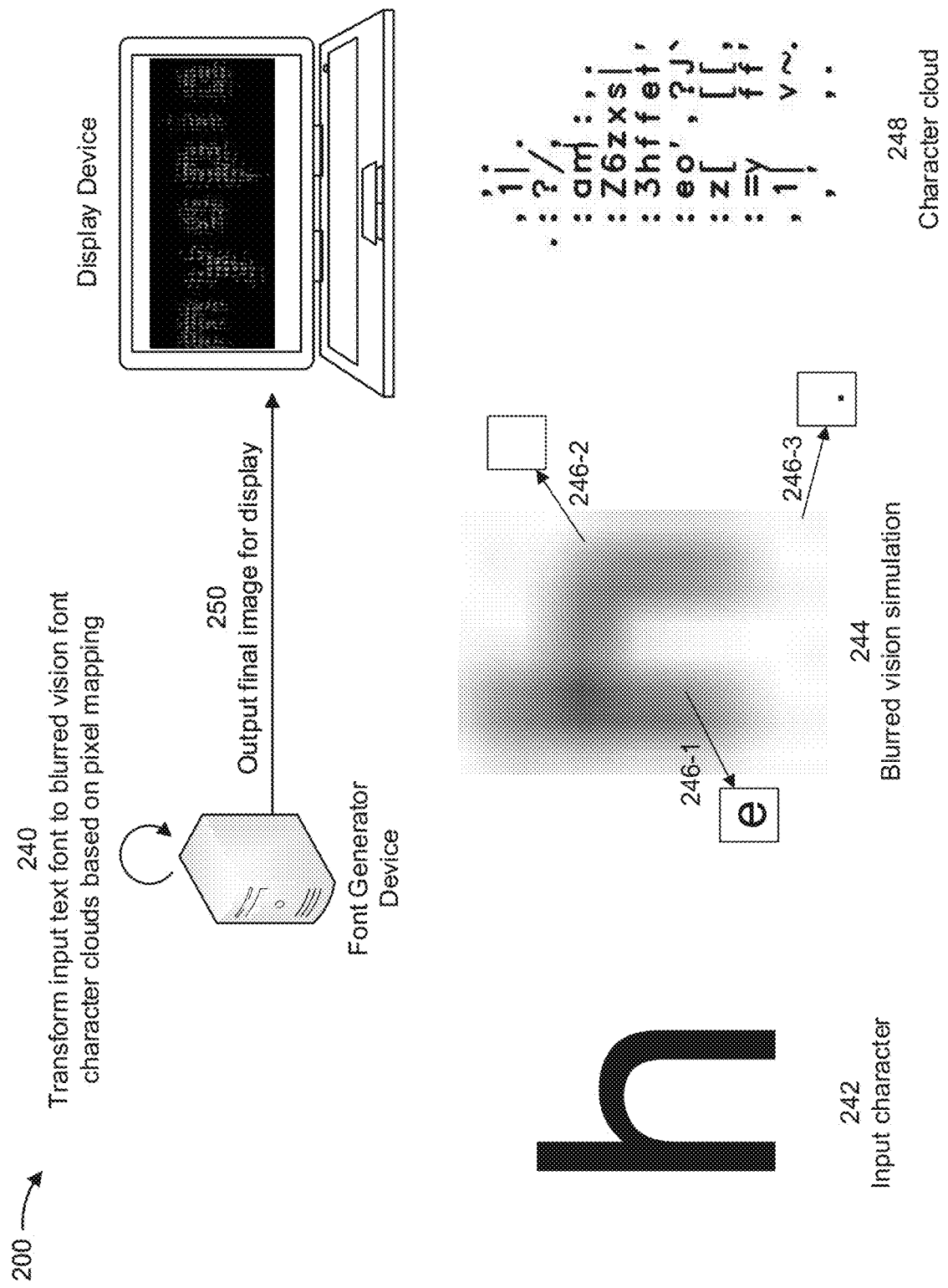

As shown in FIG. 2D, and by reference number 240, the font generator device may transform the input text font to character clouds in the blurred vision font based on a pixel mapping in cases where the readability check indicates that the input text font is readable by users with uncorrected blurred vision. For example, as described herein, each character cloud in the blurred vision font may be composed of one or more characters in an alternative characters list. For example, in some implementations, the alternative characters list may include lowercase letters, capital letters, numbers, symbols, and/or white spaces (e.g., "qwertyuiop [ ]asdfghjkl;'zxcvbnm,./1234567890=!@#$%^&*( )_+~' QWERTYUIOP{ }ASDFGHJKL:ZXCVBNM< >?|\" or a subset thereof). In some implementations, in order to generate the character clouds, the font generator device may calculate a metric or other value that represents a whiteness or a darkness of each character block in the alternative characters list. For example, in some implementations, the metric that represents the whiteness or darkness of each character block may include an average RGB value, where an average RGB value of 255.00 (255 red, 255 green, 255 blue) represents pure white and an average RGB value of 0.00 (0 red, 0 green, 0 blue) represents black, or the absence of color. Accordingly, the font generator device may calculate the average RGB value for each character block, where the average RGB value may represent where the character block appears in a spectrum from pure white to pure black (e.g., based on the proportion of a character block that is occupied by the character). For example, a white space may have an average RGB value of 255.0, the character "q" may have an average RGB value of 184.75 based on the proportion of a block that is occupied by the markings or strokes that make up the letter "q", the symbol "#" may have an average RGB value of 139.79 (darker than the letter "q") based on the proportion of a block that is occupied by the markings or strokes that make up the hashtag symbol, and so on.

Accordingly, based on the average RGB values or other values that represent the relative whiteness or darkness of each character in the alternative characters list, the font generator device may construct a mapping from a whitest character in the alternative characters list to a darkest character in the alternative characters list, which may be mapped to a whitest pixel and a darkest pixel in the blurred vision simulation (e.g., a white space or other character with a highest average RGB value may be mapped to a whitest pixel and a hashtag symbol or other character with a lowest average RGB value may be mapped to a darkest pixel). Additionally, or alternatively, in some implementations, the mapping may include one or more random variants. In some implementations, the font generator device may then replace each pixel in the blurred vision simulation with a character included in the alternative characters list based on the mapping from the whitest character in the alternative characters list to the darkest character in the alternative characters list. For example, the font generator device may calculate an average RGB value for each pixel in the blurred vision simulation, and may use the mapping to replace a whitest pixel in the blurred vision simulation with the whitest character in the alternative characters list, to replace a darkest pixel in the blurred vision simulation with the darkest character in the alternative characters list, and to replace every other pixel in the blurred vision simulation with an appropriate character in the alternative character list based on the relative whiteness or darkness of the pixel. For example, in FIG. 2D, reference numbers 242 through 248 illustrate an example of transforming a lowercase "h" into a character cloud is readable as a lowercase "h" to a myopic user but likely to be confusing or not easily readable from the same distance by a user without myopia or hyperopia or a user with corrected myopia or hyperopia. For example, in FIG. 2D, reference number 242 illustrates the input character in the original input font, and reference number 244 illustrates the appearance of the input character after rendering the blurred vision simulation. As further shown, reference numbers 246-1 through 246-2 correspond to respective pixels that have different average RGB values. Accordingly, in the character cloud shown by reference number 248, each pixel in the blurred vision simulation has been replaced with a character in the alternative characters list based on the relative whiteness or darkness of the pixel and the mapping from the whitest character to the darkest character in the alternative characters list.

Accordingly, as further shown in FIG. 2D, and by reference number 250, the font generator device may output a final image for display on a display device, where the final image may include one or more character clouds that correspond to input text in an original input text font. As shown, the one or more character clouds each include various characters that are spatially dispersed to represent a particular character, which may be readable to users with uncorrected blurred vision but not easily read by users with corrected blurred vision or users without blurred vision. Alternatively, rather than outputting the final image for display on a display device, the final image may be used to generate print media or other forms of media that include readable text. In this way, by generating the blurred vision font that is exclusively readable by users with uncorrected blurred vision, the blurred vision font may enable targeted messaging that is directed toward users with uncorrected blurred vision. For example, the blurred vision font may be used to render text that can be used to identify users with undiagnosed or uncorrected myopia or hyperopia (e.g., based on the users having the ability to read the text in the blurred vision font). Additionally, or alternatively, the blurred vision font may include information or messaging to solicit feedback and/or elicit behavior from users with uncorrected myopia or hyperopia, recommend treatment options and/or corrective measures that may improve visual acuity or daily functioning (e.g., recommending that a user who can read the text purchase eyeglasses or obtain an eye exam to test for myopia or hyperopia), and/or to filter out users that may not have blurred vision and/or users that have already corrected their blurred vision, among other examples.

As indicated above, FIGS. 2A-2D are provided as an example. Other examples may differ from what is described with regard to FIGS. 2A-2D.

Figure 3A:
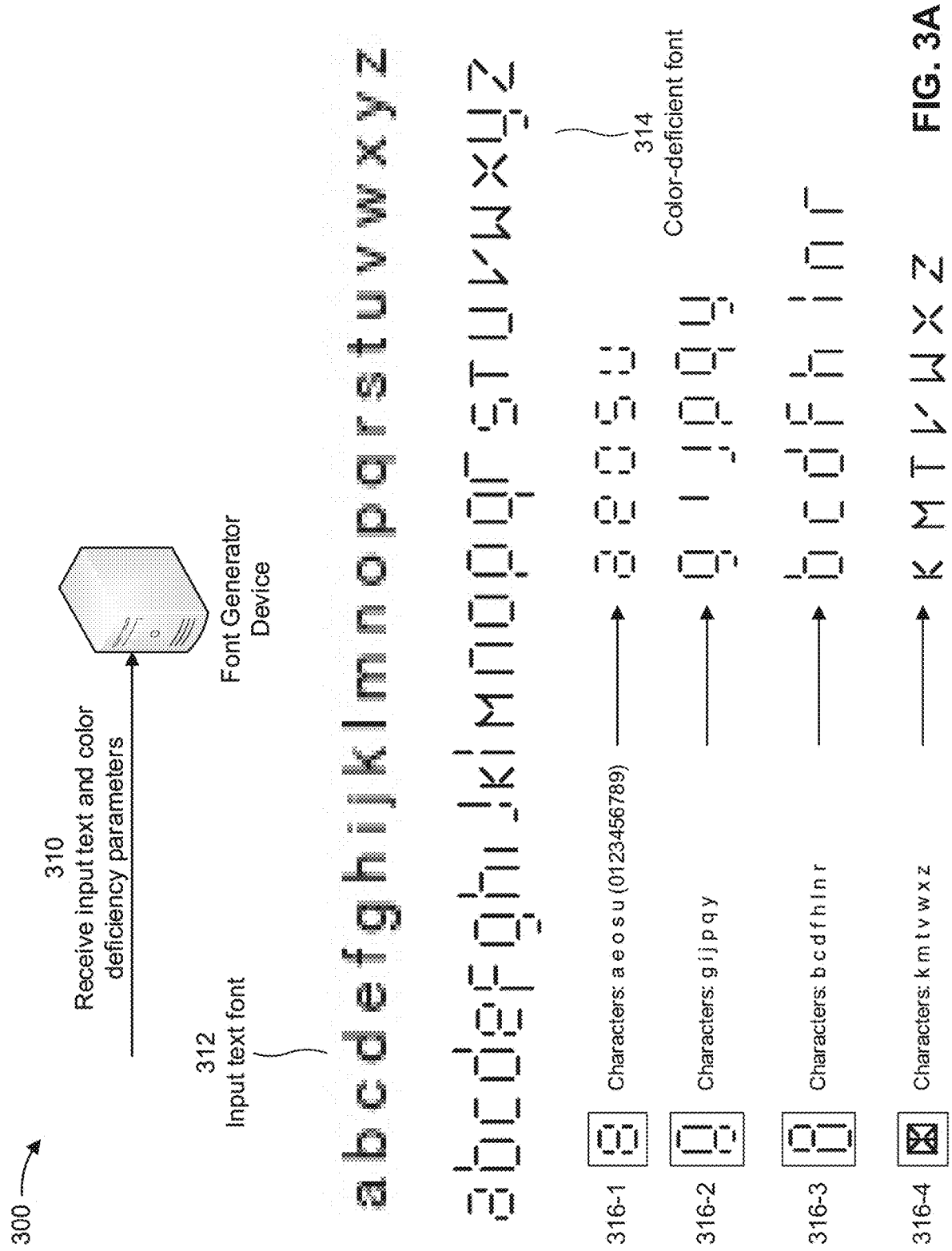
FIGS. 3A-3D are diagrams of an example implementation of a disability-oriented font generator that may generate a font that is only readable by users with a color vision deficiency.

FIGS. 3A-3D are diagrams of an example implementation 300 of a disability-oriented font generator. As shown in FIGS. 3A-3D, example implementation 300 includes a font generator device and a display device. The font generator device and the display device are described in more detail below in connection with FIG. 4 and FIG. 5. In general, as described herein, the font generator device that may generate a font that is only readable by users with a specific color vision deficiency (e.g., a type of color blindness, such as deuteranopia, protanopia, or tritanopia), and the display device may present an image in which one or more character templates are rendered over a background color using one or more color combinations that make the text depicted in the image readable exclusively by users with a specific color vision deficiency. For example, according to some estimates, around 8 percent of white males are born with a color vision deficiency, compared to less than one percent of females of all ethnicities (e.g., because the genes responsible for most common forms of color blindness are carried on the X chromosome). Color blindness can lead to challenges in carrying out various tasks that are routine for people who can see and differentiate color, such as identifying ripe fruit or rotten food and/or reading traffic lights. In addition, color blindness can lead to educational challenges and/or may need to be detected in order to verify that a person is eligible for certain jobs (e.g., aircraft pilots). Although there is usually no cure for color blindness, people with color deficiencies often learn to adapt and/or may use specialty glasses or contact lenses that can enhance color vision and minimize color vision deficiencies, which can have life-changing effects for patients that have difficulty performing daily activities because of color vision deficiencies. Accordingly, the font generator device described herein may be configured to generate the color-deficient font that is only readable by users with a specific color vision deficiency in order to aid with recognizing or identifying (e.g., diagnosing) users with color vision deficiencies and/or delivering targeted messaging to users with color vision deficiencies. However, it will be appreciated that the techniques described herein may be similarly applied to generate a color-deficient font that is readable by users with any suitable type of color vision deficiency, which may include color blindness and/or impaired or impacted color vision caused by other factors such as presence in a pure monochromatic light environment associated with a primary color deficiency, among other examples For example, as shown in FIG. 3A, and by reference number 310, the font generator device may receive input text and one or more color vision deficiency parameters that are used to generate a color-deficient font in which to present the input text. In some implementations, as shown by reference number 312, the input text may include a text string that is presented in an original font, or the input to the font generator device may include an image that contains the text string presented in the original input text font. As described in further detail herein, and as shown by reference number 314, the font generator device may generate the color-deficient font as various character templates that each have the potential to represent multiple different characters depending on how the character templates are colored. For example, as shown, the character templates may include a first character template 316-1 that includes various strokes shaped like the number 8 on a digital clock, where the first character template 316-1 may be used to represent any number or any letter in the set {a, e, o, s, u}. In another example, a second character template 316-2 includes various strokes shaped like the number 8 with an elongated upper loop, where the first character template 316-2 may be used to represent any letter in the set {g, i, j, p, q, y}. In other examples, character template 316-3 may be a vertically flipped version of character template 316-2, which may be used to represent any letter in the set {b, c, d, f, h, l, n, r}, and character template 316-4 may include various strokes shaped like an asterisk enclosed within a box, which may be used to represent any letter in the set {k, m, t, v, w, x, z}. Furthermore, in some implementations, the color vision deficiency parameters may include a color vision deficiency type (e.g., a color blindness type, such as deuteranopia, tritanopia, or protanopia, or information identifying a type of color vision impact) and a background color for the color-deficient font. For example, the color vision deficiency type may be associated with a color space that defines how certain colors in a "normal" color space (e.g., a color space representing the vision of a person with no color vision deficiencies) appear to a person with that type of color vision deficiency.

Figure 3B:
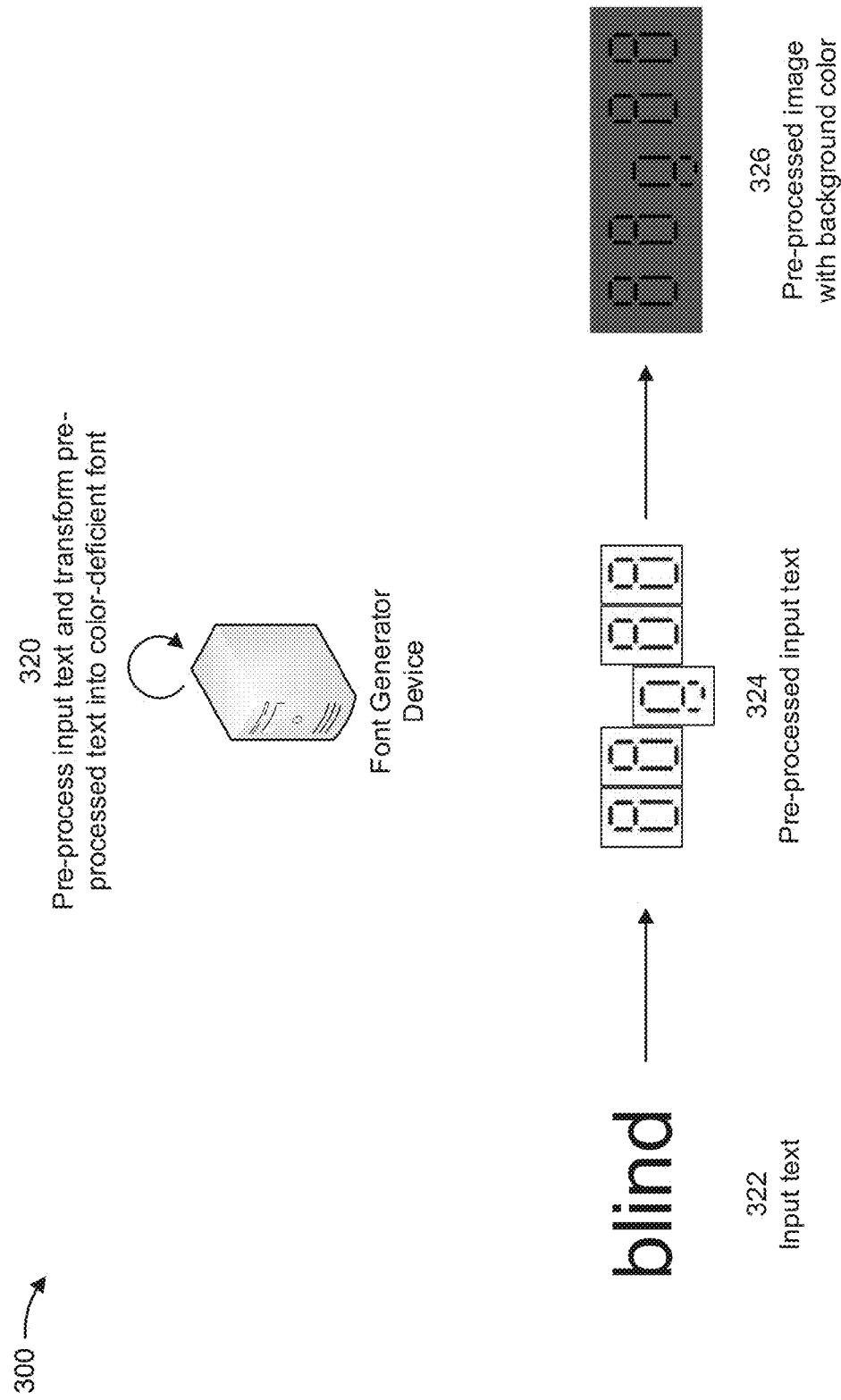

Accordingly, as described herein, each character in the input text may be mapped to one of the character templates 316, and one or more colors in a first color group and one or more colors in a second color group may be used to color the various strokes of the character templates such that the text in the final image is exclusively readable by users with the specific type of color vision deficiency. For example, as shown in FIG. 3B, and by reference number 320, the font generator device may pre-process the input text and transform each character in the pre-processed input text into the color-deficient font. For example, as shown by reference numbers 322 and 324, the input text may include the word "blind", which may be mapped to five respective character templates that are associated with each respective character. For example, referring to the example character templates in FIG. 3A, the letters "b", "l", "n", and "d" are each included in the set of characters that can be represented using character template 316-3, and the letter "i" is included in the set of characters that can be represented using character template 316-2. Accordingly, the pre-processed input text includes four instances of character template 316-3 and one instance of character template 316-2, which are arranged in a sequence such that the five character templates can later be colored in a way that spells out the word "blind". Furthermore, as shown by reference number 326, the font generator device may generate a pre-processed image in which the pre-processed text is rendered over the background color that is input to or selected by the font generator device as a color vision deficiency parameter.

Figure 3C:
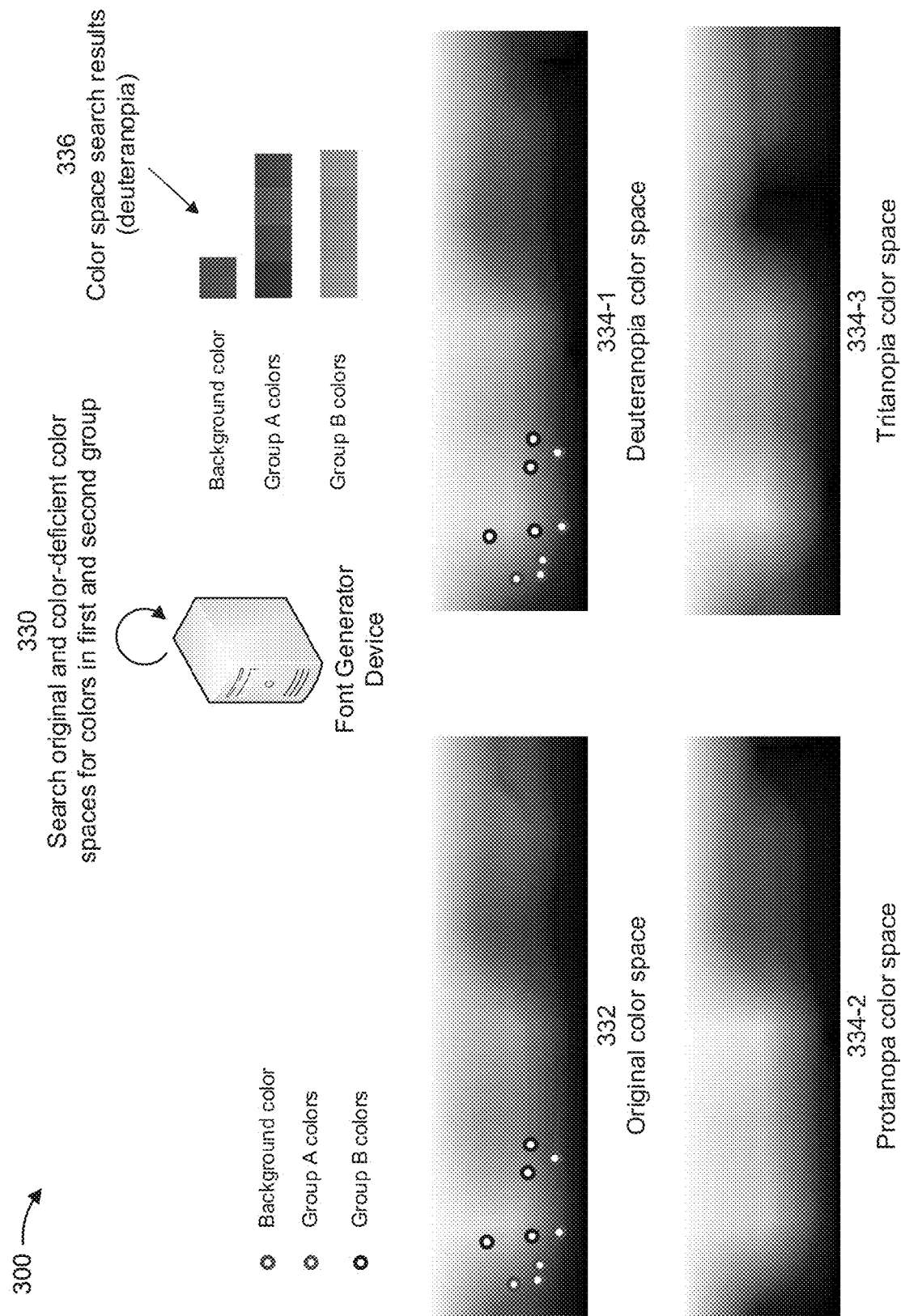

As shown in FIG. 3C, and by reference number 330, the font generator device may search an original or normal color space and a color space associated with the targeted type of color vision deficiency to identify one or more colors to include in a first color group and one or more colors to include in a second color group. For example, as shown by reference number 332, the original or normal color space may represent the vision of a person with no color vision deficiencies, and the font generator device may be configured with one or more color-deficient color spaces 334 that represent the corresponding vision of a person with a specific type of color vision deficiency. For example, reference number 334-1 represents a deuteranopia color space, where a person with deuteranopia is generally green-blind and has a decreased ability to see or distinguish red and green pigments. Accordingly, as shown, areas in the original color space 332 that are colored red or green have a yellow tint in the deuteranopia color space 334-1. In another example, reference number 334-2 represents a protanopia color space, where a person with protanopia is generally red-blind and only has cones that absorb blue and green light. Accordingly, as shown, areas in the original color space 332 that are colored red appear similar to adjacent colors (e.g., yellow or blue) in the protanopia color space 334-2. In another example, reference number 334-3 represents a tritanopia color space, where a person with tritanopia has a decreased ability to see or distinguish blue and yellow pigments. Accordingly, as shown, areas in the original color space 332 that are colored blue or yellow are associated with a different color or no color in the tritanopia color space 334-3. In other examples, the color-deficient color spaces 334 may be associated with other suitable color vision deficiencies, such as the colors that would be perceived (or not perceived) in an environment such as a darkroom where red or amber safelights are used to avoid producing light with wavelengths that may affect certain types of photographic paper.

Accordingly, in some implementations, the font generator device may search the original color space 332 and the color-deficient color space 334 associated with the targeted type of color vision deficiency to identify, based on the background color, one or more colors to include in the first color group and one or more colors to include in the second color group. For example, in some implementations, the font generator device may search the original color space 332 and the color-deficient color space 334 to identify one or more colors that are close to the background color in the color-deficient color space 334 but distinguishable from the background color in the original color space 332 (shown in FIG. 3C as "Group A" colors). In addition, the font generator device may search the original color space 332 and the color-deficient color space 334 to identify one or more colors that are distinguishable from the background color in the color-deficient color space 334 and distinguishable from the background color in the original color space 332 (shown in FIG. 3C as "Group B" colors). For example, reference number 336 illustrates example results of searching the original color space 332 and the deuteranopia color space 334-1 based on a particular background color. Furthermore, from the perspective of a user with the targeted type of color vision deficiency (e.g., deuteranopia in the illustrated example), the colors in the first color group may be indistinguishable from one another, and the colors in the first color group may be indistinguishable from one another, which makes the final output image more readable by a user with the targeted type of color vision deficiency. Furthermore, a person with no color vision deficiency or a different type of color vision deficiency may be able to distinguish the colors within a color group, which makes the final output image less readable by a user with no color vision deficiency or a different type of color vision deficiency.

Figure 3D:
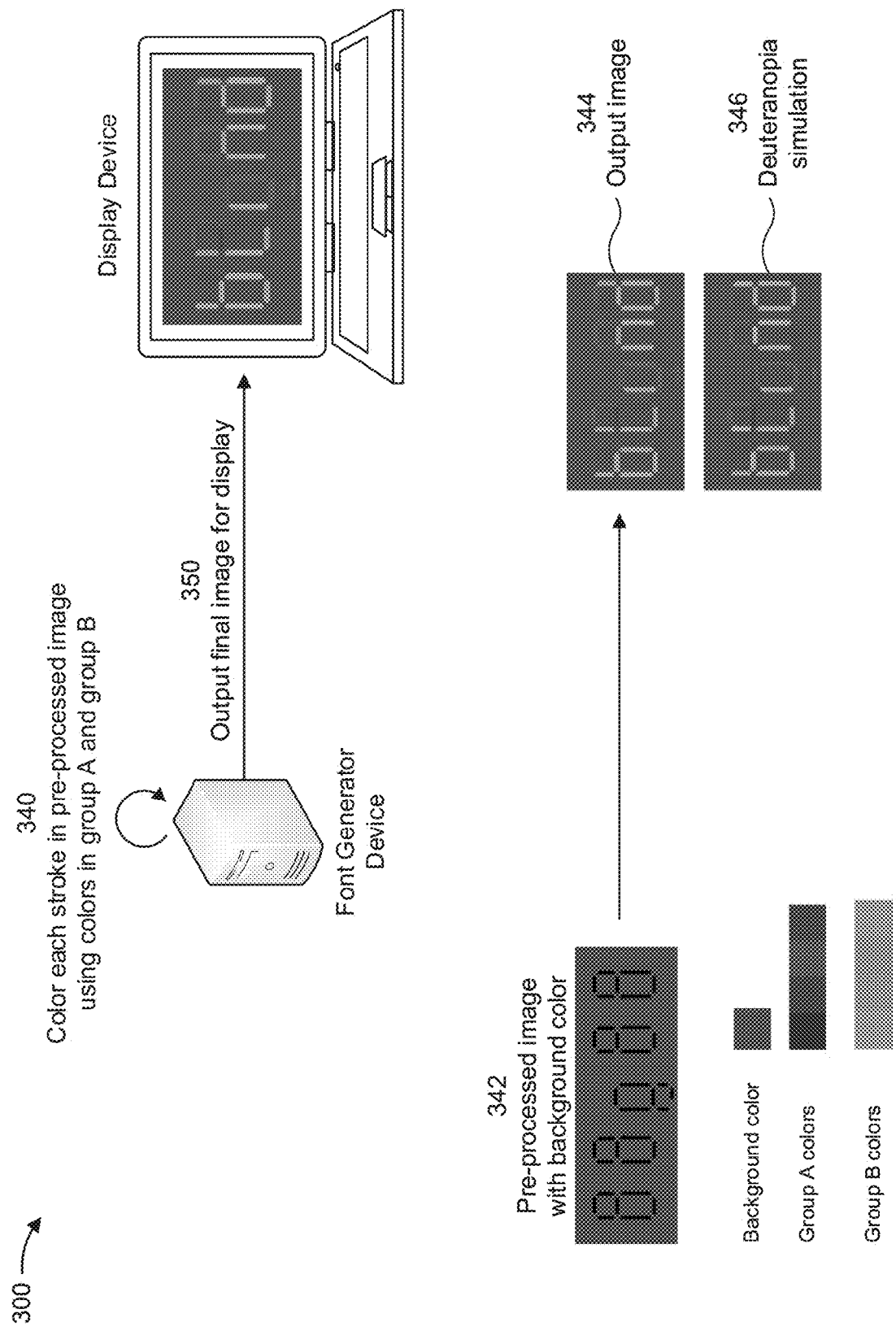

As shown in FIG. 3D, and by reference number 340, the font generator device may color each stroke in the pre-processed image using the colors in the first color group and the colors in the second color group. For example, as described above, the colors in the first color group are indistinguishable from the background color in the color-deficient color space 334 but distinguishable from the background color in the original color space 332. Accordingly, in some implementations, the colors in the first color group may be used to color one or more strokes in the character templates that are to blend in with the background color. Furthermore, because the colors in the first second group are distinguishable from the background color in the color-deficient color space 334 and distinguishable from the background color in the original color space 332, the colors in the second color group may be used to color one or more strokes in the character templates that are to correspond to a depicted character. For example, reference number 342 illustrates the pre-processed image that is created by mapping individual characters in the input text string to respective character templates and rendering the character templates over the selected and/or input background color. Furthermore, reference number 344 illustrates a final output image that may be generated by the font generator device after coloring the various strokes in the pre-processed image using the colors in the first color group and the second color group. As shown by reference number 344, the colors in the first color group and the colors in the second color group are distinguishable from the background color in a normal color space, whereby the text in the output image 344 is difficult to decipher for a person without deuteranopia. However, as further shown by reference number 346, which is a deuteranopia simulation of the output image 344, the word "blind" is clearly readable for a person with deuteranopia.

Accordingly, as further shown in FIG. 3D, and by reference number 350, the font generator device may output a final image for display on a display device, where the final image may include the output image in which one or more character templates that are mapped to respective characters in an input text string are presented over a background color with various strokes colored using colors in different color groups that are selected to make the final text readable only by users with a specific type of color vision deficiency. Alternatively, rather than outputting the final image for display on the display device, the final image may be used to generate print media or other forms of media that include text rendered in the color-deficient font. In this way, by generating the color-deficient font that is exclusively readable by users with a specific type of color vision deficiency, the color-deficient font may enable targeted messaging that is directed toward users with the specific type of color vision deficiency. For example, the color-deficient font may be used to render text that can be used to identify users with undiagnosed color blindness (e.g., based on the users having the ability to read the text in the color-deficient font). Additionally, or alternatively, the color-deficient font may include information or messaging to solicit feedback and/or elicit behavior from users with the specific color vision deficiency, recommend treatment options and/or measures that may improve color vision or daily functioning (e.g., recommending that a user who can read the text purchase specialty lenses that can improve color vision or learn adaptation techniques to compensate for color blindness), and/or to filter out users that may not have color blindness and/or users that may have a different type of color vision deficiency, among other examples.

As indicated above, FIGS. 3A-3D are provided as an example. Other examples may differ from what is described with regard to FIGS. 3A-3D.

Figure 4:
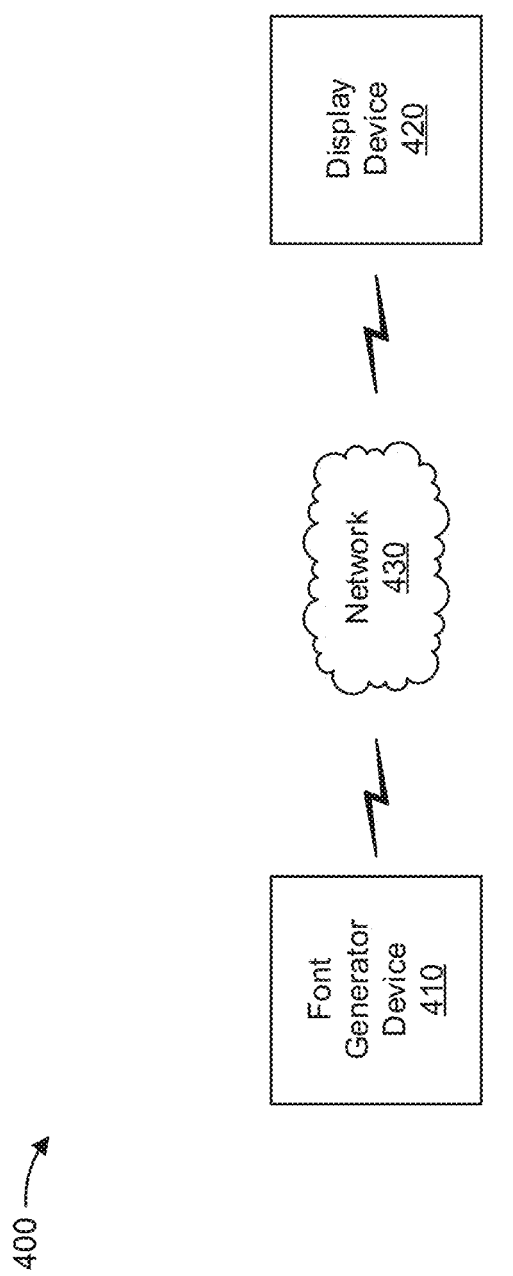
FIG. 4 is a diagram of an example environment in which systems and/or methods described herein may be implemented.

FIG. 4 is a diagram of an example environment 400 in which systems and/or methods described herein may be implemented. As shown in FIG. 4, environment 400 may include a font generator device 410, a display device 420, and a network 430. Devices of environment 400 may interconnect via wired connections, wireless connections, or a combination of wired and wireless connections.

The font generator device 410 includes one or more devices capable of receiving, generating, storing, processing, providing, and/or routing information associated with a disability-oriented font, such as a font that is only readable by users with a specific vision deficiency (e.g., myopia, hyperopia, and/or color blindness), as described elsewhere herein. The font generator device 410 may include a communication device and/or a computing device. For example, the font generator device 410 may include a server, such as an application server, a client server, a web server, a database server, a host server, a proxy server, a virtual server (e.g., executing on computing hardware), or a server in a cloud computing system. In some implementations, the font generator device 410 includes computing hardware used in a cloud computing environment. Additionally, or alternatively, the font generator device 410 may include a user device or a client device, such as a wireless communication device, a mobile phone, a user equipment, a laptop computer, a tablet computer, a desktop computer, a gaming console, a set-top box, a wearable communication device (e.g., a smart wristwatch, a pair of smart eyeglasses, a head mounted display, or a virtual reality headset), or a similar type of device.

The display device 420 includes one or more devices capable of receiving, generating, storing, processing, providing, and/or displaying information associated with a disability-oriented font, such as a font that is only readable by users with a specific vision deficiency (e.g., myopia, hyperopia, and/or color blindness), as described elsewhere herein. The display device 420 may include any suitable digital or analog display that can present visual content that may include text or images rendered in a disability-oriented font. For example, the display device 420 may include a cathode ray tube (CRT) display, a liquid crystal display (LCDs), a light-emitting diode (LED) or an organic LED (OLED) display, a plasma display, a touchscreen display, a virtual reality headset, and/or a billboard display, among other examples.

The network 430 includes one or more wired and/or wireless networks. For example, the network 430 may include a wireless wide area network (e.g., a cellular network or a public land mobile network), a local area network (e.g., a wired local area network or a wireless local area network (WLAN), such as a Wi-Fi network), a personal area network (e.g., a Bluetooth network), a near-field communication network, a telephone network, a private network, the Internet, and/or a combination of these or other types of networks. The network 430 enables communication among the devices of environment 400.

The number and arrangement of devices and networks shown in FIG. 4 are provided as an example. In practice, there may be additional devices and/or networks, fewer devices and/or networks, different devices and/or networks, or differently arranged devices and/or networks than those shown in FIG. 4. Furthermore, two or more devices shown in FIG. 4 may be implemented within a single device, or a single device shown in FIG. 4 may be implemented as multiple, distributed devices. Additionally, or alternatively, a set of devices (e.g., one or more devices) of environment 400 may perform one or more functions described as being performed by another set of devices of environment 400.

Figure 5:
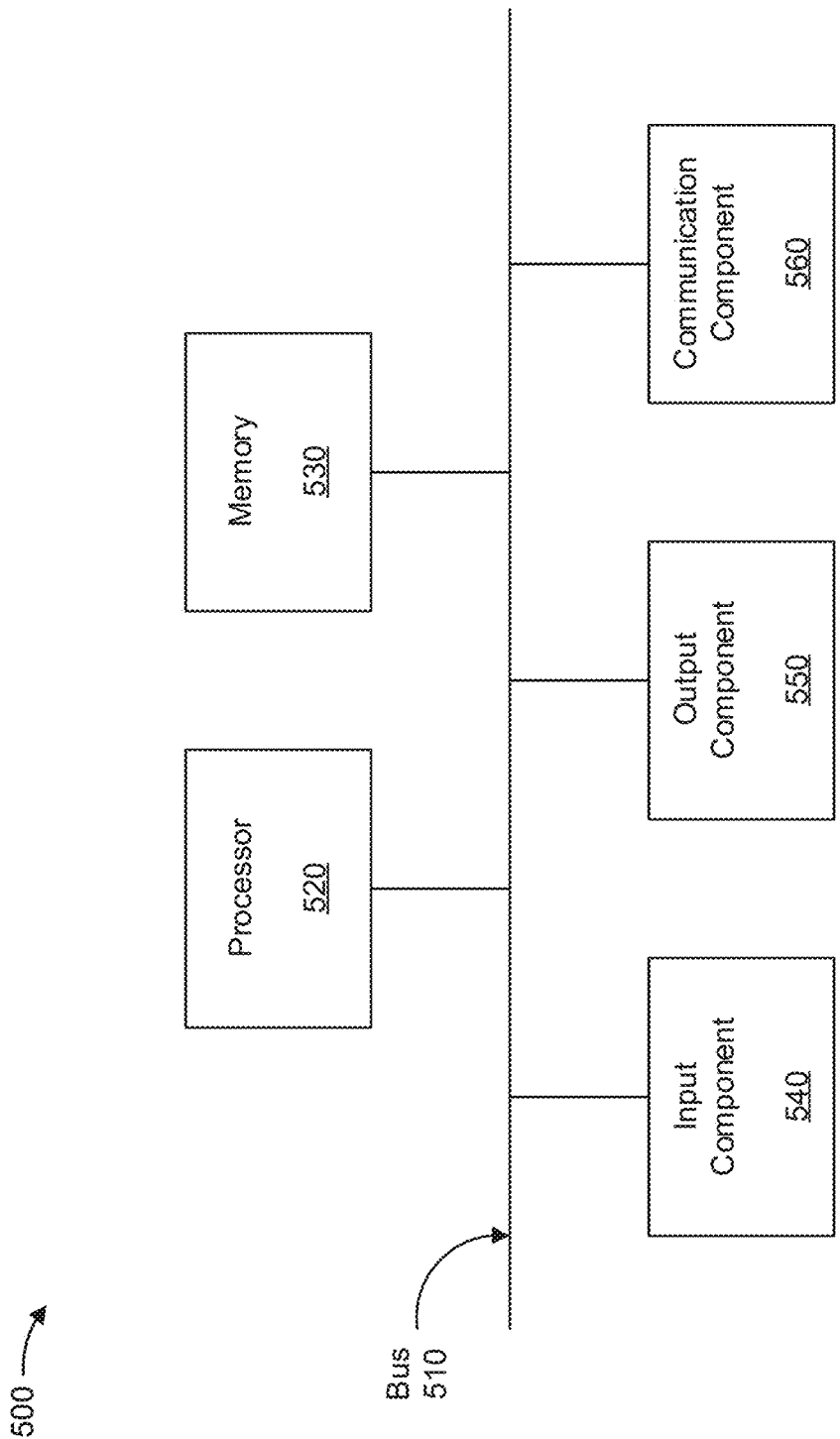
FIG. 5 is a diagram of example components of one or more devices of FIG. 4.

FIG. 5 is a diagram of example components of a device 500, which may correspond to font generator device 410 and/or display device 420. In some implementations, the font generator device 410 and/or the display device 420 include one or more devices 500 and/or one or more components of device 500. As shown in FIG. 5, device 500 may include a bus 510, a processor 520, a memory 530, an input component 540, an output component 550, and a communication component 560.

Bus 510 includes one or more components that enable wired and/or wireless communication among the components of device 500. Bus 510 may couple together two or more components of FIG. 5, such as via operative coupling, communicative coupling, electronic coupling, and/or electric coupling. Processor 520 includes a central processing unit, a graphics processing unit, a microprocessor, a controller, a microcontroller, a digital signal processor, a field-programmable gate array, an application-specific integrated circuit, and/or another type of processing component. Processor 520 is implemented in hardware, firmware, or a combination of hardware and software. In some implementations, processor 520 includes one or more processors capable of being programmed to perform one or more operations or processes described elsewhere herein.

Memory 530 includes volatile and/or nonvolatile memory. For example, memory 530 may include random access memory (RAM), read only memory (ROM), a hard disk drive, and/or another type of memory (e.g., a flash memory, a magnetic memory, and/or an optical memory). Memory 530 may include internal memory (e.g., RAM, ROM, or a hard disk drive) and/or removable memory (e.g., removable via a universal serial bus connection). Memory 530 may be a non-transitory computer-readable medium. Memory 530 stores information, instructions, and/or software (e.g., one or more software applications) related to the operation of device 500. In some implementations, memory 530 includes one or more memories that are coupled to one or more processors (e.g., processor 520), such as via bus 510.

Input component 540 enables device 500 to receive input, such as user input and/or sensed input. For example, input component 540 may include a touch screen, a keyboard, a keypad, a mouse, a button, a microphone, a switch, a sensor, a global positioning system sensor, an accelerometer, a gyroscope, and/or an actuator. Output component 550 enables device 500 to provide output, such as via a display, a speaker, and/or a light-emitting diode. Communication component 560 enables device 500 to communicate with other devices via a wired connection and/or a wireless connection. For example, communication component 560 may include a receiver, a transmitter, a transceiver, a modem, a network interface card, and/or an antenna.

Device 500 may perform one or more operations or processes described herein. For example, a non-transitory computer-readable medium (e.g., memory 530) may store a set of instructions (e.g., one or more instructions or code) for execution by processor 520. Processor 520 may execute the set of instructions to perform one or more operations or processes described herein. In some implementations, execution of the set of instructions, by one or more processors 520, causes the one or more processors 520 and/or the device 500 to perform one or more operations or processes described herein. In some implementations, hardwired circuitry is used instead of or in combination with the instructions to perform one or more operations or processes described herein. Additionally, or alternatively, processor 520 may be configured to perform one or more operations or processes described herein. Thus, implementations described herein are not limited to any specific combination of hardware circuitry and software.

The number and arrangement of components shown in FIG. 5 are provided as an example. Device 500 may include additional components, fewer components, different components, or differently arranged components than those shown in FIG. 5. Additionally, or alternatively, a set of components (e.g., one or more components) of device 500 may perform one or more functions described as being performed by another set of components of device 500.

FIG. 6 is a flowchart of an example process 600 relating to a disability-oriented font generator that may generate a font that is only readable by users with a visual deficiency. In some implementations, one or more process blocks of FIG. 6 are performed by a font generator device (e.g., font generator device 410). In some implementations, one or more process blocks of FIG. 6 are performed by another device or a group of devices separate from or including the font generator device, such as a display device (e.g., display device 420). Additionally, or alternatively, one or more process blocks of FIG. 6 may be performed by one or more components of device 500, such as processor 520, memory 530, input component 540, output component 550, and/or communication component 560.

As shown in FIG. 6, process 600 may include receiving input text that includes one or more characters (block 610). For example, the font generator device may receive input text that includes one or more characters, as described above.

As further shown in FIG. 6, process 600 may include generating a disability-oriented font based on one or more parameters that relate to a vision deficiency (block 620). For example, the font generator device may generate a disability-oriented font based on one or more parameters that relate to a vision deficiency, as described above. In some implementations, the disability-oriented font is readable by users that have the vision deficiency and unreadable by users that do not have the vision deficiency/

As further shown in FIG. 6, process 600 may include transforming the one or more characters included in the input text into the disability-oriented font (block 630). For example, the font generator device may transform the one or more characters included in the input text into the disability-oriented font, as described above.

As further shown in FIG. 6, process 600 may include generating an output that represents the input text using the disability-oriented font based on transforming the one or more characters included in the input text into the disability-oriented font (block 640). For example, the font generator device may generate an output that represents the input text using the disability-oriented font based on transforming the one or more characters included in the input text into the disability-oriented font, as described above.

Process 600 may include additional implementations, such as any single implementation or any combination of implementations described below and/or in connection with one or more other processes described elsewhere herein.

In a first implementation, the vision deficiency is blurred vision and the disability-oriented font includes one or more character clouds that are generated to be readable only by users with uncorrected blurred vision.

In a second implementation, alone or in combination with the first implementation, the one or more parameters used to generate the disability-oriented font include an original font associated with the input text and one or more of an alternative character list, a character cloud stroke thickness, or a character cloud spacing associated with the one or more character clouds.

In a third implementation, alone or in combination with one or more of the first and second implementations, process 600 includes rendering a blurred vision simulation on the input text using the original font, and determining, based on the blurred vision simulation, whether the input text is readable by users with uncorrected blurred vision, wherein the one or more characters included in the input text are transformed into the disability-oriented font based on determining that the input text is readable in the original font by users with uncorrected blurred vision.

In a fourth implementation, alone or in combination with one or more of the first through third implementations, generating the disability-oriented font includes calculating, for each character in an alternative character list associated with the one or more character clouds, a value that represents a darkness of the respective character, and generating, based on the value that represents the darkness of each respective character in the alternative character list, a mapping from a whitest character in the alternative character list to a darkest character in the alternative character list.

In a fifth implementation, alone or in combination with one or more of the first through fourth implementations, transforming the one or more characters included in the input text into the disability-oriented font includes rendering a blurred vision simulation on the input text using an input font, and replacing each pixel in the blurred vision simulation with a character included in the alternative character list based on the mapping from the whitest character in the alternative character list to the darkest character in the alternative character list.

In a sixth implementation, alone or in combination with one or more of the first through fifth implementations, the vision deficiency is a color deficiency and the disability-oriented font includes a first color group and a second color group that are selected based on a background color and a color deficiency type.

In a seventh implementation, alone or in combination with one or more of the first through sixth implementations, generating the disability-oriented font includes searching a normal color space and a color-deficient color space associated with the color deficiency type to identify the first color group and the second color group, wherein the first color group includes one or more colors that are visually indistinct from the background color in the color-deficient color space and visually distinct from the background color in the normal color space, and wherein the second color group includes one or more colors that are visually distinct from the background color in the color-deficient color space and visually distinct from the background color in the normal color space.

In an eighth implementation, alone or in combination with one or more of the first through seventh implementations, transforming the one or more characters included in the input text into the disability-oriented font includes converting each character included in the input text into a character template associated with a respective character list, wherein the character template includes a set of strokes to represent different characters included in the character list associated with the character template, coloring a first portion of the set of strokes included in each respective character template using one or more colors in the first color group, and coloring a second portion of the set of strokes included in each respective character template using one or more colors in the second color group.

In a ninth implementation, alone or in combination with one or more of the first through eighth implementations, the color deficiency type is deuteranopia, protanopia, or tritanopia.

Although FIG. 6 shows example blocks of process 600, in some implementations, process 600 includes additional blocks, fewer blocks, different blocks, or differently arranged blocks than those depicted in FIG. 6. Additionally, or alternatively, two or more of the blocks of process 600 may be performed in parallel.

The foregoing disclosure provides illustration and description, but is not intended to be exhaustive or to limit the implementations to the precise forms disclosed. Modifications may be made in light of the above disclosure or may be acquired from practice of the implementations.

As used herein, the term "component" is intended to be broadly construed as hardware, firmware, or a combination of hardware and software. It will be apparent that systems and/or methods described herein may be implemented in different forms of hardware, firmware, and/or a combination of hardware and software. The actual specialized control hardware or software code used to implement these systems and/or methods is not limiting of the implementations. Thus, the operation and behavior of the systems and/or methods are described herein without reference to specific software code—it being understood that software and hardware can be used to implement the systems and/or methods based on the description herein.

As used herein, satisfying a threshold may, depending on the context, refer to a value being greater than the threshold, greater than or equal to the threshold, less than the threshold, less than or equal to the threshold, equal to the threshold, not equal to the threshold, or the like.

Although particular combinations of features are recited in the claims and/or disclosed in the specification, these combinations are not intended to limit the disclosure of various implementations. In fact, many of these features may be combined in ways not specifically recited in the claims and/or disclosed in the specification. Although each dependent claim listed below may directly depend on only one claim, the disclosure of various implementations includes each dependent claim in combination with every other claim in the claim set. As used herein, a phrase referring to "at least one of" a list of items refers to any combination of those items, including single members. As an example, "at least one of: a, b, or c" is intended to cover a, b, c, a-b, a-c, b-c, and a-b-c, as well as any combination with multiple of the same item.

No element, act, or instruction used herein should be construed as critical or essential unless explicitly described as such. Also, as used herein, the articles "a" and "an" are intended to include one or more items, and may be used interchangeably with "one or more." Further, as used herein, the article "the" is intended to include one or more items referenced in connection with the article "the" and may be used interchangeably with "the one or more." Furthermore, as used herein, the term "set" is intended to include one or more items (e.g., related items, unrelated items, or a combination of related and unrelated items), and may be used interchangeably with "one or more." Where only one item is intended, the phrase "only one" or similar language is used. Also, as used herein, the terms "has," "have," "having," or the like are intended to be open-ended terms. Further, the phrase "based on" is intended to mean "based, at least in part, on" unless explicitly stated otherwise. Also, as used herein, the term "or" is intended to be inclusive when used in a series and may be used interchangeably with "and/or," unless explicitly stated otherwise (e.g., if used in combination with "either" or "only one of").

What is claimed is:

1. A method, comprising:
    receiving, by a font generator device, input text that includes one or more characters;
    generating, by the font generator device and using a machine learning model and one or more parameters that relate to a vision deficiency, an output that indicates a predicted interpretation of the input text by users that have the vision deficiency, wherein the vision deficiency is blurred vision;
    generating, by the font generator device and based on the output, a disability-oriented font based on the one or more parameters that relate to the vision deficiency, wherein the disability-oriented font is readable by users that have the vision deficiency from a predetermined distance and unreadable by users that do not have the vision deficiency from the predetermined distance;
    transforming, by the font generator device, the one or more characters included in the input text into the disability-oriented font, wherein transforming the one or more characters of the input text into the disability-oriented font includes:
        generating a blurred vision simulation on the input text using by applying one or more image processing techniques to the input text;
        generating a mapping for each character in an alternative character list with a respective pixel in the blurred vision simulation such that a whitest character in the alternative character list is mapped to a whitest pixel in the blurred vision simulation and a darkest character in the alternative character list is mapped to a darkest pixel in the blurred vision simulation, wherein the alternative character list includes a set of characters reflecting appearance of characters to the users that have the vision deficiency; and replacing each pixel in the blurred vision simulation with a respective character in the alternative character list based on the mapping such that the whitest pixel in the blurred vision simulation is replaced with the whitest character in the alternative character list and the darkest pixel in the blurred vision simulation is replaced with the darkest character in the alternative character list;

generating, by the font generator device, an output image that represents the input text using the disability-oriented font based on transforming the one or more characters included in the input text into the disability-oriented font;

receiving, by the font generator device, a first feedback from a first user based on the output image; and outputting, by the font generator device, recommendations to improve the vision deficiency, to a user device associated with the first user, based on the first feedback.

2. The method of claim 1, wherein the disability-oriented font includes one or more character clouds that represent an original font of the one or more characters based on a darkness or whiteness in each pixel of an image that reflects the blurred vision simulation on the input text to the users that have the vision deficiency.

3. The method of claim 2, wherein the one or more parameters that relate to the vision deficiency include the original font associated with the input text and one or more of the alternative character list, a character cloud stroke thickness, or a character cloud spacing associated with the one or more character clouds.

4. The method of claim 3, further comprising:
rendering the blurred vision simulation on the input text using the original font; and
determining, based on the blurred vision simulation, whether the input text is readable by the users that have the vision deficiency, wherein the one or more characters included in the input text are transformed into the disability-oriented font based on determining that the input text is readable in the original font by the users that have the vision deficiency.

5. The method of claim 2, wherein generating the disability-oriented font includes:
calculating, for each character in the alternative character list associated with the one or more character clouds, a value that represents a darkness of a respective character in the alternative character list; and
generating, based on the value that represents the darkness of each respective character in the alternative character list, the mapping.

6. The method of claim 1, further comprising:
determining a confidence level in the predicted interpretation of the input text;
comparing the determined confidence level with a threshold confidence level; and
generating the disability-oriented font based on the determined confidence level that exceeds the threshold confidence level.

7. The method of claim 1, wherein the alternative character list includes at least one of lowercase letters, uppercase letters, numbers, symbols, or a blank space.

8. The method of claim 1, wherein the recommendations include information related to at least one of treatment options for the first user or corrective measures for the vision deficiency of the first user.

9. The method of claim 1, further comprising:
receiving, by the font generator device, a second feedback from a second user based on the output image;
determining that the second user is without the vision deficiency based on the second feedback; and
outputting, by the font generator device, information related to filter out the second user, based on the determination that the second user is without the vision deficiency.

10. A font generator device, comprising:
one or more memories; and
one or more processors, coupled to the one or more memories, configured to:
receive input text that includes one or more characters;
generate, using a machine learning model and on one or more parameters that relate to a vision deficiency, an output that indicates a predicted interpretation of the input text by users that have the vision deficiency, wherein the vision deficiency is blurred vision;
generate, based on the output, a disability-oriented font based on the one or more parameters that relate to the vision deficiency,
wherein the disability-oriented font is readable by users that have the vision deficiency from a predetermined distance and unreadable by users that do not have the vision deficiency from the predetermined distance;
transform the one or more characters included in the input text into the disability-oriented font, wherein the one or more processors, to transform the one or more characters of the input text into the disability-oriented font, are configured to:
generate a blurred vision simulation on the input text using by applying one or more image processing techniques to the input text;
generate a mapping for each character in an alternative character list with a respective pixel in the blurred vision simulation such that a whitest character in the alternative character list is mapped to a whitest pixel in the blurred vision simulation and a darkest character in the alternative character list is mapped to a darkest pixel in the blurred vision simulation, wherein the alternative character list includes a set of characters reflecting appearance of characters to the users that have the vision deficiency; and
replace each pixel in the blurred vision simulation with a respective character in the alternative character list based on the mapping such that the whitest pixel in the blurred vision simulation is replaced with the whitest character in the alternative character list and the darkest pixel in the blurred vision simulation is replaced with the darkest character in the alternative character list;
generate content that is targeted at users that have the vision deficiency,
wherein the content includes an output image that represents the input text using the disability-oriented font that is readable only by users that have the vision deficiency and unreadable by users that do not have the vision deficiency;

receive feedback from a user based on the output image; and output recommendations to improve the vision deficiency, to a user device associated with the user, based on the feedback.

11. The font generator device of claim 10, wherein the disability-oriented font includes one or more character clouds that represent an original font of the one or more characters based on a darkness or whiteness in each pixel of an image that reflects the blurred vision simulation on the input text to the users that have the vision deficiency based on the one or more parameters.

12. The font generator device of claim 11, wherein the one or more processors, to generate the disability-oriented font, are configured to:

calculate, for each character in the alternative character list associated with the one or more character clouds, a value that represents a darkness of a respective character in the alternative character list; and generate, based on the value that represents the darkness of each respective character in the alternative character list, the mapping.

13. The font generator device of claim 11, wherein the one or more parameters that relate to the vision deficiency include the original font associated with the input text and one or more of the alternative character list, a character cloud stroke thickness, or a character cloud spacing associated with the one or more character clouds.

14. The font generator device of claim 13, wherein the one or more processors are further configured to:

render the blurred vision simulation on the input text using the original font; and determine, based on the blurred vision simulation, whether the input text is readable by the users that have the vision deficiency, wherein the one or more characters included in the input text are transformed into the disability-oriented font based on determining that the input text is readable in the original font by the users that have the vision deficiency.

15. The font generator device of claim 10, wherein the one or more processors are further configured to:

determine a confidence level in the predicted interpretation of the input text;

compare the determined confidence level with a threshold confidence level; and generate the disability-oriented font based on the determined confidence level that exceeds the threshold confidence level.

16. A non-transitory computer-readable medium storing a set of instructions, the set of instructions comprising:

one or more instructions that, when executed by one or more processors of a font generator device, cause the font generator device to:

receive input text that includes one or more characters;

generate, using a machine learning model and on one or more parameters that relate to a vision deficiency, an output that indicates a predicted interpretation of the input text by users with the vision deficiency, wherein the vision deficiency is blurred vision;

generate, based on the output, a disability-oriented font based on the one or more parameters that relate to the vision deficiency, wherein the disability-oriented font is readable by users that have the vision deficiency from a predetermined distance and unreadable by users that do not have the vision deficiency from the predetermined distance;

transform the one or more characters included in the input text into the disability-oriented font, wherein the one or more characters of the input text is transformed into the disability-oriented font by:

generating a blurred vision simulation on the input text using by applying one or more image processing techniques to the input text;

generating a mapping for each character in an alternative character list with a respective pixel in the blurred vision simulation such that a whitest character in the alternative character list is mapped to a whitest pixel in the blurred vision simulation and a darkest character in the alternative character list is mapped to a darkest pixel in the blurred vision simulation, wherein the alternative character list includes a set of characters reflecting appearance of characters to the users that have the vision deficiency; and replacing each pixel in the blurred vision simulation with a respective character in the alternative character list based on the mapping such that the whitest pixel in the blurred vision simulation is replaced with the whitest character in the alternative character list and the darkest pixel in the blurred vision simulation is replaced with the darkest character in the alternative character list;

generate an output image to identify one or more users that have the vision deficiency by representing the input text using the disability-oriented font based on transforming the one or more characters included in the input text into the disability-oriented font;

receiving feedback from a user based on the output image; and outputting recommendations to improve the vision deficiency, to a user device associated with the user, based on the feedback.

17. The non-transitory computer-readable medium of claim 16, wherein the disability-oriented font includes one or more character clouds that represent an original font of the one or more characters based on a darkness or whiteness in each pixel of an image that reflects the blurred vision simulation on the input text to the users that have the vision deficiency.

18. The non-transitory computer-readable medium of claim 17, wherein the one or more parameters that relate to the vision deficiency include the original font associated with the input text and one or more of the alternative character list, a character cloud stroke thickness, or a character cloud spacing associated with the one or more character clouds.

19. The non-transitory computer-readable medium of claim 18, wherein the set of instructions are further comprising:

rendering the blurred vision simulation on the input text using the original font; and determining, based on the blurred vision simulation, whether the input text is readable by the users that have the vision deficiency, wherein the one or more characters included in the input text are transformed into the disability-oriented font based on determining that the input text is readable in the original font by the users that have the vision deficiency.

20. The non-transitory computer-readable medium of claim 16, wherein the set of instructions are further comprising:

determine a confidence level in the predicted interpretation of the input text;

compare the determined confidence level with a threshold confidence level; and generate the disability-oriented font based on the determined confidence level that exceeds the threshold confidence level.

\* \* \* \* \*